US008956541B2

(12) United States Patent
Elliott

(10) Patent No.: US 8,956,541 B2
(45) Date of Patent: Feb. 17, 2015

(54) COMPOSITION AND METHOD FOR RETENTION OF SOLVATED COMPOUNDS AND IONS

(71) Applicant: Eco Verde Technologies, Inc., Fort Lauderdale, FL (US)

(72) Inventor: Curtis Elliott, Royal Palm Beach, FL (US)

(73) Assignee: Eco Verde Technologies, Inc., Pembroke Pines, FL (US)

(*) Notice: Subject to any disclaimer, the term of this patent is extended or adjusted under 35 U.S.C. 154(b) by 0 days.

(21) Appl. No.: 13/913,852

(22) Filed: Jun. 10, 2013

(65) Prior Publication Data
US 2013/0331268 A1 Dec. 12, 2013

Related U.S. Application Data

(60) Provisional application No. 61/660,885, filed on Jun. 18, 2012.

(51) Int. Cl.
A01N 25/10 (2006.01)
C02F 1/28 (2006.01)
C02F 1/42 (2006.01)
B01J 20/26 (2006.01)
C08G 65/26 (2006.01)
C08G 8/22 (2006.01)
C08G 8/36 (2006.01)
B01J 20/32 (2006.01)
B09C 1/00 (2006.01)
C09D 161/14 (2006.01)
C02F 1/68 (2006.01)
C08G 8/38 (2006.01)
C09D 161/12 (2006.01)
C02F 103/08 (2006.01)
B09C 1/08 (2006.01)
C02F 3/00 (2006.01)
C02F 103/06 (2006.01)

(52) U.S. Cl.
CPC ............ A01N 25/10 (2013.01); C02F 2103/08 (2013.01); B01J 20/262 (2013.01); B09C 1/08 (2013.01); C02F 3/00 (2013.01); C02F 1/285 (2013.01); C08G 65/2612 (2013.01); C08G 8/22 (2013.01); C08G 8/36 (2013.01); C02F 2103/06 (2013.01); B01J 20/3272 (2013.01); B09C 1/002 (2013.01); C09D 161/14 (2013.01); C02F 1/688 (2013.01); C08G 8/38 (2013.01); C09D 161/12 (2013.01)
USPC ........... 210/681; 210/691; 210/747; 424/405; 424/406; 514/275

(58) Field of Classification Search
USPC .................. 210/681, 691, 747; 424/405, 406; 514/275
See application file for complete search history.

(56) References Cited

U.S. PATENT DOCUMENTS

| 3,010,919 | A | 11/1961 | MacKinney et al. |
| 3,025,255 | A | 3/1962 | Lambuth |
| 3,156,670 | A | 11/1964 | Soldatos |
| 3,725,349 | A | 4/1973 | Smith et al. |
| 3,857,815 | A | 12/1974 | Smith et al. |
| 4,157,324 | A | 6/1979 | Culbertson |
| 4,221,873 | A | 9/1980 | Volodko et al. |
| 5,420,312 | A | 5/1995 | Andrews et al. |
| 5,603,834 | A | 2/1997 | Rogers et al. |
| 5,888,397 | A | 3/1999 | Rogers et al. |
| 6,811,703 | B2 | 11/2004 | Elliott |
| 2004/0195182 | A1* | 10/2004 | Elliott ........................... 210/681 |
| 2005/0082511 | A1 | 4/2005 | Poellmann et al. |

OTHER PUBLICATIONS

Bostick et al. (Separation Science and Technology, 32(1-4), pp. 793-811, 1997).*
Johnson et al. (Phenol-Formaldeyde Resin Structure for hte Synthesis of Glassy Carbon, 479-479. 1997).*
A. Pizzi, "Wood Adhesives", Chemistry and Technology 1989, vol. 2, Chapter 7, pp. 191-193.
Lisperguer J. et al., "Differential Scanning Calorimetry and Dinamic Mechanical Analysis of Phenol-Resorcinol Formaldehyde Resins", J. Chil. Chem. Soc., vol. 50, N. 2 (Jun. 2005), pp. 451-453.
Dodiuk, H. et al., "Handbook of Thermoset Plastics", PDL Handbook Series, Third Edition (2014), pp. 37-38.
Definition of "Partition Ratio." International Union of Pure and Applied Chemistry's Gold Book. Obtained Jun. 5, 2014 from <http://goldbook.iupac.org/P04440.html>.
Guenet, Jean-Michel , "Polymer-Solvent Molecular Compounds", Elsevier First Edition 2008, pp. 172-173 (4 pages).
Tanaka, Shunsuke et al., "Morphology Control of Ordered Mesoporous Carbon Using Organic-Templating Approach", http://www.intechopen.com/books/progress-in-molecular-and-environmental-bioengineering-from-analysis-and-modeling-to-technology-applications/morphology-control-of-ordered-mesoporous-carbon-using-organic-templating-approach (14 page), Aug. 2011.
United States Golf Association, , "USGA Recommendations for a Green Construction", 2004 (11 Pages).
Yang, Guichun et al., "Novel Synthesis of Monoethers of Hydroquinone and Polymer-Supports", Synthetic Communications, vol. 32, No. 23, pp. 3637-3642, 2002 (6 Pages).
"File History of US 3,857,815", (62 pages), Dec. 30, 1974.

(Continued)

Primary Examiner — Anoop Singh
Assistant Examiner — Anna Falkowitz
(74) Attorney, Agent, or Firm — Dorsey & Whitney LLP; Lori Sarageno

(57) ABSTRACT

Storage stable polyhydroxylated aromatic ether adducts of polyalkylene oxide are described. Reactive compositions are formed by combining an ether adduct with an aldehyde, optionally further adding a phenolic-aldehyde prepolymer. The reactive compositions are cured by removing water, by acidification, or both. The cured compositions sorb solvated compounds from environments containing water. The cured compositions are also useful for pre-loading with compounds that are subsequently released at a controlled rate into environments containing water.

20 Claims, 7 Drawing Sheets

(56) References Cited

OTHER PUBLICATIONS

Durairaj, Raj B., "Resorcinol Based Resins and Applications", *"Resorcinol: Chemistry, Technology and Applications"*, 2005, pp. 179-185 (9 pages).

Guenet, Jean-Michel, "Polymer-Solvent Molecular Compounds", *Elsevier, First Edition* 2008, pp. 172-173 (4 pages).

Hamming, Lesley M. et al., "Fouling Resistant Biomimetic Poly(Ethylene Glycol) Based Grafted Polymer Coatings", *Sigma-Aldrich, Material Matters* 2008, 3.3, 52. Accessed Nov. 28, 2011. (5 pages).

Johnson, K. K. et al., "Phenol-Formaldeyde Resin Structures for the Synthesis of Glassy Carbon", *NYS School of Ceramic Engineering and Material Science at Alfred University Alfred*, MY 14802, pp. 478-479, (2 pages).

Karuppannasamy, S. et al., "Reactions of Phenols and Alcohols over Thoria: Mechanism of Ether Formation", *Journal of Catalysis 66*, 1980, pp. 281-289 (9 pages).

Pekala, R. W., "Organic aerogels from the polycondensation of resorcinol with formaldehyde", *Journal of Materals Science* 24 (1989) 3221-3227 (7 pages).

Rogers, Robin D. et al., "Novel Polyethylene Glycol-Based Aqueous Biphasic Systems for the Extraction of Strontium and Cesium", *Separation Science and Technology*, 30(7-9), pp. 1203-1217, 1995 (17 pages).

Tanaka, Shunsuke et al., "Morphology Control of Ordered Mesoporous Carbon Using Organic-Templating Approach", http://www.intechopen.com/books/progress-in-molecular-and-environmental-bioengineering-from-analysis-and-modeling-to-technology-applications/morphology-control-of-ordered-mesoporous-carbon-using-organic-templating-approach (14 page), Aug. 2011.

United States Golf Association, "USGA Recommendations For a Green Construction", 2004 (11 pages).

Yang, Guichun et al., "Novel Synthesis of Monoethers of Hydroquinone and Resorcinol on Soluble Polymer-Supports", *Synthetic Communications*, vol. 32, No. 23, pp. 3637-3642, 2002 (6 pages).

\* cited by examiner

COMPOSITION AND METHOD FOR RETENTION OF SOLVATED COMPOUNDS AND IONS

PRIORITY

This application claims the benefit of U.S. Provisional Application Ser. No. 61/660,885, entitled "Composition and Method for Retention of Solvated Compounds and Ions", filed Jun. 18, 2012, which application is hereby incorporated by reference in its entirety.

BACKGROUND

A number of compositions and methods have been developed to reduce the concentration of solvated compounds and ions from liquid water or environments containing liquid water. Such compositions and methods are desirable for use in water remediation applications including sewage or wastewater treatment; removal of leacheates such as excess fertilizers, pesticides, herbicides, or nematicides from groundwater sources, particularly where a high rate of percolation of such compounds is known; remediation of leacheates from e.g. landfill areas or industrial streams carrying toxins or other hazardous waste; desalinization of seawater; treatment of municipal water sources; and the like.

Many conventional water remediation compositions and methods are of limited use in one or more agricultural and industrial processes where such water remediation is needed. Limitations of conventional technologies include inability to maintain dimensional stability and integrity during use, compositional instability before or during use, foaming during processing or in use, water solubility (too hydrophilic) or insufficient wettability (too hydrophobic), high viscosity leading to difficulties in processing and/or use, pH sensitivity, and limited ranges of compounds that can be sorbed/retained by the composition due to inherent chemical incompatibilities. In some cases, the cost of a conventional technology is prohibitive.

Conventional technologies include microorganism-based or plant-based treatments; use of impermeable membranes to collect leacheates and runoff for subsequent treatment at a remote treatment/separation facility, oxidation lagoon, and the like; use of adsorbents such as activated carbon, silica, silicates, alumina, and synthetic zeolites and clays to capture compounds; solid phase extraction (affinity-based chromatographic techniques and materials) using compositions such as alkylated silicas or other functionalized silicas or functionalized clays, and the like; and combinations of these technologies.

Water holding enhancement and ion exchange capacities in a water remediation composition are also beneficial but are generally lacking in the conventional methods and compositions. For example, superabsorbent polymers (SAP) are useful for water retention in soil, for example, but due to their hydrophilic or even hygroscopic nature they are not typically useful for removal of organic compounds from a remediation environment. Further, as most SAP rely on ionic groups such as polyacrylate salts to provide the hygroscopic character of the polymers, the presence of ionic content in the water reduces the ability of the SAP to swell and retain water as compared to the same SAP in a substantially ion-free environment.

The conventional technologies for water remediation and water retention are not generally suitable for carrying out the slow and/or controlled release of organic compounds. Such release is advantageously employed for e.g. fertilizers, pesticides, herbicides, or nematicides, wherein the composition is "preloaded" with a compound, then the preloaded composition is applied to soil for release of the compound. Slow release compositions are highly desirable in agricultural applications for preventing leaching out or runoff of the chemicals, where such compositions are capable of release of one or more chemicals of interest at a targeted rate. The targeted rate, for example, can be commensurate with the rate of absorption by a particular plant or group of plants. In such cases, the affinity of the composition for the compound to be released is key to its release properties. However, most conventional technologies such as those listed above are simply not useful or practicable for such "reverse" uses as slow and/or controlled release of chemicals into a selected environment.

One material that is suitable for both water remediation and slow release of compounds in agricultural applications is described by Elliott, U.S. Pat. No. 6,811,703 ("Elliott"). Elliott teaches compositions and methods related to the reaction of a methylolated dialkyl diphenol with a monoalkyl ether adduct of a polyalkylene oxide bromide to yield a polyalkylene oxide adduct of the methylolated dialkyl diphenol, or polyoxyetheralkyldiphenol. The adduct is then employed in a reaction with a phenolic aldehyde prepolymer either in an aqueous environment or on a solid support, relying on the methylol moieties of the adduct to achieve the reaction with the phenolic aldehyde prepolymer. The compositions can be used directly, or sprayed and cured on a particulate solid support, for water remediation. Once applied to the remediation environment, the crosslinked network polymer is effective at reducing and retaining a plethora of organic compounds. Additionally, the crosslinked composition adheres to ion exchange compositions such as clays, enabling scavenging of ionic entities from the remediation environment.

Once the phenolic aldehyde is mixed with the adduct, the crosslinking reaction takes place at commonly employed storage temperatures (e.g. between 0° C. and 30° C.) leading to a limited shelf life. Because of this reactivity, application of the composition to the remediation environment, or spraying the composition onto the surface of a particulate, must be carried out within a few days of mixing the adduct with the prepolymer.

Additionally, a preferred diphenol starting material in the compositions of Elliott is bisphenol A (4-[2-(4-hydroxyphenyl)propan-2-yl]phenol), a suspected xenoestrogen that has been associated medically with organizational changes in the prostate, breast, testis, mammary glands, body size, brain structure and chemistry, and behavior of laboratory animals. Where bisphenol A is employed, it is methylolated by reacting the bisphenol with formaldehyde, a known carcinogen. Both bisphenol A and formaldehyde are considered undesirable compounds in the industry and thus suitable replacements or alternative materials are actively sought.

Smith et al., U.S. Pat. No. 3,857,815 ("Smith") teaches a polypropylene glycol or polybutylene glycol modified phenolic aldehyde resole. Resoles are phenol formaldehyde resins having a ratio of formaldehyde to phenol of at least 1 and typically about 1.5. The materials of Smith are formed by blending a phenolic aldehyde with polyalkylene glycol plus aniline or m-hydroxyaniline, then curing with excess formaldehyde. There is no evidence that the polyalkylene glycol undergoes any reaction with the resole, nor would one of skill expect any reaction between the hydroxyl-terminated alkylene glycol and the resole to occur under the conditions set forth by Smith. Rather, it would appear that the polylkylene glycol is merely an additive that, depending on molecular weight, becomes entangled or entrapped within the resole, analogous to a semi-interpenetrating network. Such formulations are unsuitable for use in water remediation applications. The remediation environment would cause the polyalkylene glycol to leach out of the crosslinked resole network. Such leaching provides instability during use in a water containing environment.

There is a need for water remediation compositions that are environmentally benign; do not require the use of bisphenol A or excess formaldehyde; are effective for retention of a wide variety of organic compounds, ionic content, or both in environments containing liquid water; are storage stable in a convenient form, from which the final product can be easily prepared; have water retention properties; are stable in their intended use environment; and can be used for their slow release or controlled release properties, for example in timed release of chemicals commonly employed in agriculture.

SUMMARY

We have found that aromatic compounds having at least two hydroxyl groups bonded directly on the same aromatic moiety are reacted with polyalkylene oxide monoethers to yield the corresponding ether adducts of the polyhydroxylated aromatic compounds; and that these ether adducts are reactive with phenolic aldehyde prepolymers to result in crosslinked networks useful as water remediation compositions and/or controlled release compositions. The polyhydroxylated aromatic compounds useful in forming the compositions of the invention do not require methylolation to incur reactivity with the phenolic aldehyde prepolymer; thus, a reduction of the amount of formaldehyde employed in forming the network is realized when compared to similar reaction schemes employing methylolated adducts of polyalkylene oxides. Additionally, the reactivity of polyhydroxylated aromatic compounds to aldehyde-mediated crosslinking is much greater than that of the reactivity of monohydroxylated aromatic compounds such as phenol; similarly, the corresponding ether adducts of polyhydroxylated aromatic compounds are more reactive to aldehyde-mediated crosslinking than their monohydroxylated ether adduct counterparts. The crosslinking reaction does not require the use of bisphenol A or other alkyl diphenols, although such alkyl diphenols are optionally employed.

The ether adduct is formed by reacting a polyhydroxylated aromatic compound with a functionalized polyalkylene oxide (PAO), for example a PAO bromide, tosylate, mesitylate, nosylate, brosylate, or epoxide. Various PAOs and their copolymers and blends are useful in forming the ether adducts.

The ether adducts are shelf-stable. The shelf life of the ether adducts is more than a month, or up to one year or even more than one year. Yet when blended with a phenolic aldehyde prepolymer to form a reactive composition, the ether adducts give rise to rapid crosslinking. Once the reactive composition is formed, the crosslinking reaction proceeds without the need for additional curing steps, such as heating, to yield a cured composition of the invention. However, drying, acidification, and/or heating is often carried out using any of a number of conventional techniques, in order to form a commercially useful end product as will be described in more detail herein. Where drying and/or heating is carried out, the composition is dried and heated alone, e.g. in film or droplet form; or on a substrate such as a carrier film or particle.

In embodiments, the cured compositions are water remediation compositions and/or controlled release compositions.

In an alternative embodiment, a polyhydroxylated aromatic compound is pre-reacted with a methylolated dialkyl diphenol, and the reaction product thereof is then reacted with the functionalized PAO. The resulting diphenol-functional ether adducts are capable of participating in crosslinking and bonding reactions with phenolic aldehyde prepolymers upon blending and subsequent activation, similarly to the above described crosslinking and bonding reactions and with similar advantages of long shelf life prior to blending the diphenol-functional ether adducts with the phenolic aldehyde prepolymers.

In another alternative embodiment, an amount of formaldehyde is reacted with a polyhydroxylated aromatic compound or a mixture of polyhydroxylated aromatic compounds to yield dimers, trimers, and/or higher oligomers of the polyhydroxylated aromatic compound or mixture thereof via condensation. The oligomers are then reacted with functionalized PAO, wherein one or more PAO chains are bonded to the oligomers. The resulting oligomeric ether adducts are capable of participating in crosslinking and bonding reactions with phenolic aldehyde prepolymers upon blending and subsequent activation, similarly to the above described crosslinking and bonding reactions and with similar advantages of long shelf life.

DETAILED DESCRIPTION

A. Definitions

Figure 1:
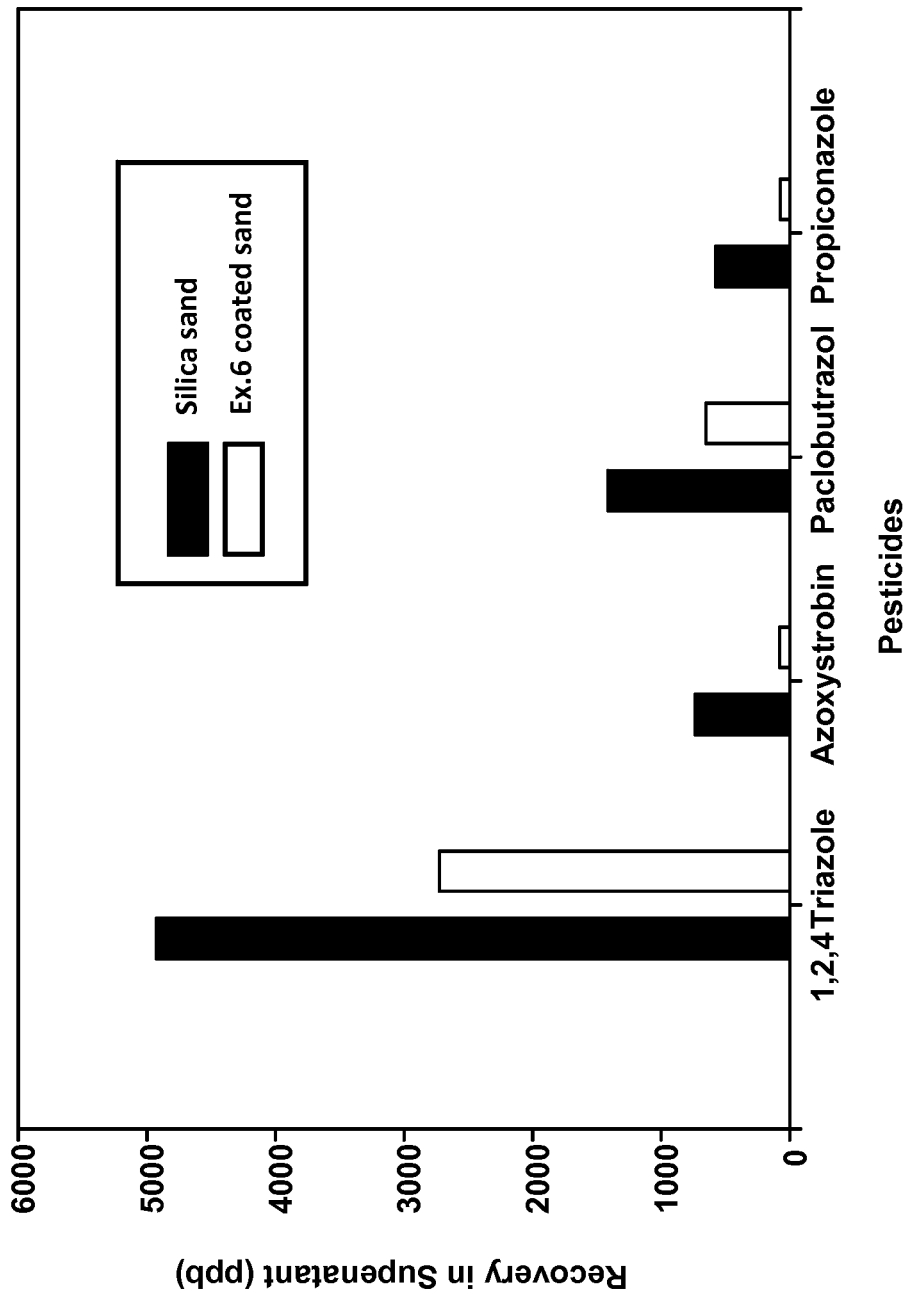
FIG. 1 is a plot of the recovery from supernatant of four different pesticides after contacting solutions of the pesticides with either silica sand or a composition of the invention.

For the purposes of this disclosure, the term "polyhydroxylated aromatic compound" means an aromatic compound having two or more hydroxyl groups situated on the same aromatic moiety and bonded directly thereto, that is, the oxygen of the hydroxyl is bonded to a carbon within the aromatic moiety. In some embodiments, at least two of the hydroxyl groups are situated such that conjugative interactions activate or facilitate electron pair donation between them. The definition includes one or more such aromatic moieties; that is, multiple polyhydroxylated aromatic moieties can be bonded together, with conjugation between aromatic moieties being optional, provided that each aromatic moiety has at least two hydroxyl groups situated on the same aromatic moiety and bonded directly thereto. In some embodiments the polyhydroxylated aromatic compound has one or more additional substituents bonded thereto.

For the purposes of this disclosure, the term "ether adduct" means a compound having the structure

wherein X is the residue of a polyhydroxylated aromatic compound, O is oxygen, and Y is a group containing at least 10 polyalkylene oxide repeat units.

For the purposes of this disclosure, the term "phenolic aldehyde prepolymer" means a partially condensed product of a phenolic compound or mixture of phenolic compounds, and an aldehyde or mixture of aldehydes, wherein the phenolic compound or mixture of phenolic compounds has undergone some amount of polycondensation in the presence of the aldehyde or mixture of aldehydes, but curing is not complete. In some embodiments, the phenolic compound or mixture of phenolic compounds includes phenol, resorcinol, or a mixture thereof; and the aldehyde is formaldehyde; however, it will be understood that other compositions that cure according to the known mechanisms of cure for phenolic compounds and aldehydes are included in the definition according to the invention. The phenolic aldehyde prepolymer is, in various embodiments, a solid or is provided as a solution, emulsion, or dispersion in water.

For the purposes of this disclosure, the term "reactive composition" means a mixture of an ether adduct with either a phenolic aldehyde prepolymer or an aldehyde, prior to any substantial subsequent condensation reaction.

For the purposes of this disclosure, the term "cured composition" means the substantially fully condensed reaction product of a reactive composition.

For the purposes of this disclosure, the term "composite composition" means a combination of the cured composition plus one or more additional elements, compounds, compositions, substrates, or combinations thereof, the combination configured to achieve remediation or release performance.

For the purposes of this disclosure, the term "ion exchange material" means any solid phase material capable of an ion-exchange reaction. Such materials include both naturally arising materials and synthetic materials.

For the purpose of this disclosure, the term "water remediation" means removal of organic, inorganic, or organometallic compounds, ionic species, microorganisms (including viruses, bacteria, and fungi), prions, parasites, or various combinations thereof, from a source of liquid water via adsorption or absorption. The source can be substantially water itself; water including one or more dissolved solutes, such as seawater; or it can be water, optionally including a dissolved solute, that is further entrained in or combined with a solid phase material, such as soil, water or a bodily fluid entrapped in a superabsorbent polymer, or water within a living organism.

For the purpose of this disclosure, the term "water remediation composition" means a cured composition in a form that is useful for water remediation applications. The water remediation composition is in some embodiments a composite composition, such as a blend, a layered form, or other suitable format. The water remediation composition may contain a minor or major fraction of the cured composition by weight or volume.

For the purpose of this disclosure, the term "remediation environment" means a location and the immediate surrounding area wherein a water remediation composition is situated, will be situated, or is intended to be situated.

For the purpose of this disclosure, the term "controlled release" means addition of organic or ionic compounds or moieties, or a combination of both, to a source of liquid water at a predictable rate of addition. The source can be substantially water itself, or it can be water entrained in or combined with a solid phase material. Examples of the latter include water in soil, water entrapped in a superabsorbent polymer, and water within a living organism.

For the purpose of this disclosure, the term "controlled release composition" means a cured composition in a form that is useful for controlled release. The controlled release composition is in some embodiments a composite composition, such as a blend, a layered form, or other suitable format. The controlled release composition may contain a minor or major fraction of the cured composition by weight or volume.

For the purpose of this disclosure, the term "release environment" means a location and the immediate surrounding area wherein a controlled release composition is situated, will be situated, or is intended to be situated.

For the purpose of this disclosure, the term "comprising" is inclusive or open-ended and does not exclude additional unrecited elements, compositional components, or method steps. Accordingly, such term is intended to be synonymous with the words "has", "have", "having", "includes", "including", and any derivatives of these words.

B. Reagents and Reactions

The following materials are advantageously employed, in various combinations, in the reactions to form the water remediation compositions of the invention. In general, the reagents are also employed to form the controlled release compositions of the invention, along with one or more compounds for controlled release that are used to impregnate the composition. One of skill will recognize that the reagents disclosed in this section are not limiting and additional variations thereof are also contemplated; and further, the particular reagents selected in any given reaction scheme are varied in type and amount according to the targeted end product and uses thereof that are envisioned.

1. Polyhydroxylated Aromatic Compounds

A reagent employed in the reactions leading to the compositions of the invention is a polyhydroxylated aromatic compound. A polyhydroxylated aromatic compound is an aromatic compound having two or more hydroxyl groups situated on the same aromatic moiety and bonded directly thereto. Preferred polyhydroxylated aromatic compounds have at least two hydroxyl groups situated such that a conjugative interaction facilitates (activates) electron pair donation to an unsubstituted aromatic carbon of the moiety. In various embodiments, one, two, or more aromatic rings are present in the polyhydroxylated aromatic compound. In some embodiments additional substituents are present on one or more rings of the polyhydroxylated aromatic compound. Blends and adducts of the polyhydroxylated aromatic compounds are also suitably employed in the reactions leading to the ether adducts as that term is defined above.

Polyhydroxylated aromatic compounds include polyhydroxylated benzenes. Useful polyhydroxylated benzene compounds include dihydroxybenzenes and trihydroxybenzenes. Dihydroxybenzene compounds useful in the reactions of the present invention include, in embodiments, hydroquinone (1,4-dihydroxybenzene), catechol (1,2-dihydroxybenzene), and resorcinol (1,3-dihydroxybenzene). Trihydroxybenzene compounds useful in the reactions of the present invention include, in embodiments, phloroglucinol (1,3,5-trihydroxybenzene), hydroxyhydroquinone (1,2,4-trihydroxybenzene), and pyrogallol (1,2,3-benzenetriol). In some embodiments, polyhydroxylated adducts of naphthalene are useful in the reactions of the present invention; examples of such compounds include, in embodiments, 1,2-dihydroxynaphthalene, 1,3-dihydroxynaphthalene, 1,6-dihydroxynaphthalene, 2,3-dihydroxynaphthalene, 2,7-dihydroxynaphthalene, and the like.

In some embodiments, other polyhydroxylated aromatic compounds are useful in the reactions and compositions of the invention. Polyhydroxylated anthracene, phenanthrene, azulene, and the like are suitably employed in the reactions that form one or more compositions of the invention. Additionally, dimers, trimers, and oligomers of polyhydroxylated aromatic compounds are useful in the reactions and compositions of the invention.

In some embodiments the polyhydroxylated aromatic compound, or a blend of polyhydroxylated aromatic compounds, are pre-condensed or oligomerized. For example, the polycondensation reaction commonly employed in forming phenolic aldehyde prepolymers is advantageously employed herein to form dimers, trimers, and higher oligomers of the polyhydroxylated aromatic compound(s). Specifically, a polyhydroxylated aromatic compound, a combination of two or more polyhydroxylated compounds, or a combination of a polyhydroxylated compound and an additional aromatic compound are combined with an amount of an aldehyde that is selected to provide the desired level of oligomerization, and an acidic or basic catalyst employed under conditions of mild heat, for example between 50° C. and 100° C., to obtain the condensation products thereof. In some embodiments, the molar ratio of aldehyde to polyhydroxylated aromatic compound employed to form an oligomer is between about 0.0005:1 to 0.8:1, or about 0.001 to 0.6:1, or about 0.1:1 to 0.4:1, or about 0.2:1 to 0.3:1. The oligomers thus formed have multiple reaction sites that are useful in subsequent steps in the formation of the ether adducts and cured compositions of the reaction, as will be readily recognized by one of skill.

Examples of additional aromatic compounds useful in such condensation reactions with one or more polyhydroxylated aromatic compounds include phenol, alkylated phenol, lignosulfonic acid, phenoldisulfonic acid, and other aromatic compounds without limitation, provided that after the condensation reaction at least some portion of the condensate includes polyhydroxylated aromatic functionality as defined above.

Additionally, other compounds having more than one polyhydroxylated aromatic moiety present therein are useful in the reactions and compositions of the invention. In some embodiments one or more of the multiple polyhydroxylated aromatic moieties are conjugated with respect to one another. In other embodiments, the polyhydroxylated aromatic moieties are not conjugated with respect to one another; some examples of such compounds include 4,4'-((1E)-1-penten-4-yne-1,5-diyl)biscatechol, quercetin (2-(3,4-dihydroxyphenyl)-3,5,7-trihydroxychromen-4-one), myricetin (3,5,7-trihydroxy-2-(3,4,5-trihydroxyphenyl)chromen-4-one), theaflavin (1,8-bis(3-alpha,5,7-trihydroxy-2-alpha-chromanyl)-5H-benzocyclohepten-5-one) and gossypol (7-(8-formyl-1,6,7-trihydroxy-3-methyl-5-propan-2-ylnaphthalen-2-yl)-2,3,8-trihydroxy-6-methyl-4-propan-2-ylnaphthalene-1-carbaldehyde).

In some embodiments, polyhydroxylated aromatic compounds include naturally occurring oligomeric structures, or oligomeric structures that are commercially available. Examples of useful oligomeric structures include tannic acid, humic acid, fulvic acid, and Quebracho extracts. In some embodiments, such oligomers are employed as the polyhydroxylated aromatic compound; in other embodiments, these oligomers are further condensed with an aldehyde, one or more additional polyhydroxylated aromatic compounds, one or more additional aromatic compounds, or a combination of two or more of these.

In some embodiments additional substituents are present on one or more rings of the polyhydroxylated aromatic compounds. For example one or more alkyl, ether, aryl, halogen, amino, amido, imino, carbonyl, carboxylate, or other substituents, or a combination of two or more thereof, may be present as substituents on the ring(s) of the polyhydroxylated aromatic compounds. Any such additional substituents are preferably electron donating (activating) substituents because in some embodiments electron withdrawing (deactivating) substituents reduce the reactivity of the polyhydroxylated aromatic compound to the crosslinking reaction with the phenolic aldehyde prepolymer. If additional substituents are present on the ring(s), then preferably either conjugative interaction or the inductive effect of the substituent facilitates electron pair donation to an aromatic carbon moiety during the crosslinking reaction. In embodiments, the substituents are not so bulky as to restrict the desired reactivity toward the reactions that are described below. In some embodiments, one or more substituents is selected to impart additional functionality to the cured composition, such as surfactancy, ion exchange capacity, compatibility with a targeted environment, or ability to partition a targeted molecule or group of molecules. In some embodiments, the additional substituent is methyl; representative embodiments include orcinol (3,5-dihydroxytoluene) and 2,5-dimethyl resorcinol. In some embodiments, the additional substituent is a $C_6$-$C_{24}$ linear or branched alkyl or alkenyl chain, wherein the presence of the hydrocarbon moiety imparts a hydrophobic locus. In some embodiments, an additional substituent is a sulfonate moiety, such as sodium, lithium, or ammonium sulfonate; or carboxylate, such as sodium, lithium, or ammonium carboxylate. Such additional substituents are also present, in some embodiments, on one or more additional aromatic compounds that are employed in a condensation reaction with one or more polyhydroxylated aromatic compounds, one or more aldehydes, or both.

Blends of two or more of any of the polyhydroxylated aromatic compounds described herein are useful in various embodiments of the invention. The use of any of the above alone or in combination is not particularly limited; rather, the selection and use thereof is suitably adjusted to result in the desired end product useful in one or more applications described herein or others that will be envisioned by one of skill.

2. Polyalkylene Oxides

Another reagent employed in the reactions leading to the products of the invention is a polyalkylene oxide (PAO). In embodiments, the PAO has structure 1:

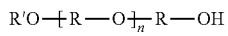

1 wherein R is a linear, branched, or cyclic alkyl or aralkyl moiety that is the same or different for each n group. In some embodiments, R has between 1 and 12 carbons. In some embodiments, R has between 2 and 6 carbons. In embodiments, R represents a random or block copolymer, terpolymer, or other copolymeric combination of R moieties. In embodiments, R is —$CH_2$—$CH_2$—, —$CH(CH_3)$—$CH_2$—, or a mixture thereof in a random or block conformation. R' is H, $CH_3$, or a linear, branched, or cyclic alkyl, aryl, aralkyl, or the like, optionally having one or more additional heteroatoms bonded thereto; and n is between about 10 and 1000, or about 25 and 750, or about 50 and 500. In some embodiments, R' is not H. In some such embodiments, R' is methyl. In other such embodiments, R' is a linear or branched alkyl chain having from 4 to 18 carbon atoms. In some embodiments, all R are —$CH_2$—$CH_2$— and n is between about 50 and 200, or about 75 and 150.

In some embodiments, the PAO is a branched structure, for example a PAO having the structure 2:

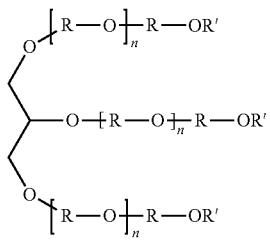

wherein the values of R, R', and n are each independently as described above with the proviso that at least one R' is H. In some such embodiments, each occurrence of n is between about 2 and 1000, or about 10 and 750, or about 25 and 500; in other embodiments, the total sum of all n is between about 10 and 5000, or about 25 and 2500, or about 50 and 1000.

Additional branched, hyperbranched, or dendritic type PAO structures are envisioned and lie within the scope of the invention, as will be appreciated by one of skill. In all such embodiments, at least one hydroxyl group attached to an alkyl moiety is present on the PAO; in some such embodiments, the linear or branched PAO has only one hydroxyl group.

It will be appreciated by the skilled artisan that the nature of the PAO, including the type and ratio of R moieties, number n of repeat units, and other variables will be optimized for specific end uses and affect the nature of water remediation or controlled release applications envisioned within the scope of the invention.

3. Ether Adducts of PAO and Polyhydroxylated Aromatic Compounds

Hydroxyl groups attached to the PAO alkyl moiet(ies) provide reactive centers for functionalization. Functionalized PAO is employed to bond the PAO to the polyhydroxylated aromatic compound to form the aromatic PAO ether adduct, as will be described in detail below. The aromatic PAO ether adduct ("ether adduct"), in turn, is the reactive moiety by which the PAO becomes incorporated into the cured compositions of the invention during the crosslinking reactions that are also described in more detail below. We have found that hydroxyl-terminated PAO itself will not undergo a reaction with phenolic aldehyde prepolymers under cure conditions; that is, the conditions that cause curing of phenolic aldehyde networks do not lead to the formation of covalent bonds between phenolic aldehyde prepolymers and PAO (hydroxyl terminated). Under such conditions the result is, at best, a semi-interpenetrating network where PAO is untethered but distributed within the phenolic aldehyde network. Untethered PAOs are unsuitable for water remediation or controlled release applications because the PAOs are not stable within the network and can, for example, migrate and leach out of the network during processing, or use, or both.

Further, and without being limited by theory, we believe that covalent bonding of the PAO within the phenolic aldehyde network is necessary for performance in many of the envisioned applications. We believe the effective prevention of phase separation between the phenolic aldehyde and PAO provided by covalent bonding between the materials leads to the observed results in sequestration, and in some cases subsequent controlled release, of various compounds. Additionally, In the case of a solute associated with a covalently bound PAO, capture or release of a solute is a function of the partition coefficient of the system. This is determined by the equilibrium concentration of solute in the ambient environment (mobile phase) and on the polymeric surface. So the specific PAO employed, as well as the bonding of crosslinked polymer matrix thereto, will serve to either capture compounds from a particular environment or provide controlled release thereof into the environment. The ability of the compositions of the invention to capture (remediate) or release compounds is also dependent on variables such as, in a water environment, the amount of water and e.g. rate of flow of water (in soil, for example, this is referred to as the percolation rate) solubility of compound in the ambient water or aqueous solution, and rate of diffusion across the surface of the crosslinked matrix.

The aromatic PAO ether adduct is the means by which the PAO is covalently bound into the polymer network and thus is a necessary aspect of the invention.

A number of different reactions are suitably employed to form the aromatic PAO ether adduct ("ether adduct"). For example, in some embodiments a simple acid catalysis, coupled with addition of heat, is sufficient to cause the condensation reaction of two alcohols—here, the polyhydroxylated aromatic compound and the hydroxyl terminated PAO—to form the corresponding ether. However, in some such embodiments acid catalyzed condensation results in the formation of unacceptable amounts of symmetrical ether products, e.g. PAO dimer. Further, in some embodiments PAOs are susceptible to cleavage in acidic environments when subjected to heat. Thus, in some embodiments it is preferable to employ reaction conditions that lead to the formation of asymmetrical ethers, more particularly the asymmetrical ether of a PAO and a polyhydroxylated aromatic compound, wherein deleterious side reactions are avoided.

In some embodiments, an effective means to form an ether bond between the PAO and the polyhydroxylated aromatic compound is described by Karuppannasamy et al., *J. Cat.* 66, 281-289 (1990), wherein thoria is employed as a catalyst that is selective for asymmetric aralkyl ether formation.

In some embodiments, Williamson ether synthesis is an effective means to form the ether bond between the PAO and the polyhydroxylated aromatic compound. Williamson ether synthesis is a known method by which asymmetric ethers are formed from alkyl bromides and alcohols. In some embodiments, the bromide intermediate for the Williamson ether synthesis is formed by reacting a PAO having an hydroxyl endgroup with phosphorus tribromide (PBr$_3$). The reaction of aliphatic alcohols with PBr$_3$ is known to result in the displacement of the hydroxyl group of the alcohol with bromine to yield the alkyl bromide product. A representative example of PAO bromide formation, followed by Williamson ether synthesis to yield the ether adduct is shown below, employing a linear monoether PAO and hydroquinone:

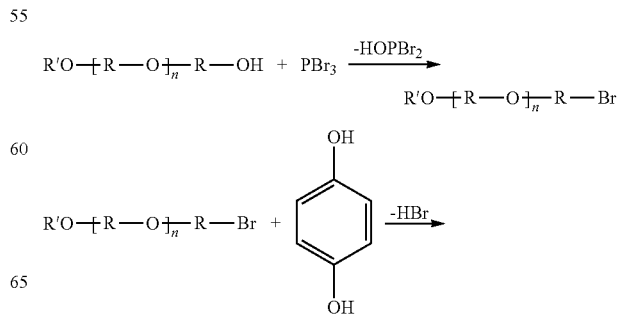

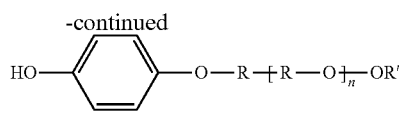

In some embodiments, both the reaction of the PAO to yield the PAO bromide intermediate and the subsequent Williamson ether synthesis are carried out using synthetic techniques generally described by Elliott, U.S. Pat. No. 6,811,703 and elsewhere employing conventional organic chemistry guidelines.

It will be appreciated that several variations of the bromide intermediate synthesis and subsequent ether adduct formation are selected in various embodiments in order to optimize the final composition for a particular application. For example, in some embodiments where two hydroxyls are present on a PAO, a monobromide or dibromide intermediate is formed. In some embodiments where the end product is a PAO dibromide, the PAO is selected to undergo two Williamson ether syntheses, leading to a diether adduct of the PAO. Similarly, in other embodiments a branched PAO having two or more hydroxyls is selected for one or more bromide intermediate syntheses and one or more ether syntheses. Similarly, in embodiments where the polyhydroxylated aromatic compound has three hydroxyl groups, one hydroxyl or two hydroxyls are selected for ether adduct formation by reaction with one or two moles of the PAO bromide intermediate per mole of PAO monobromide. More complicated schemes are also envisioned, for example wherein PAO dibromides, tribromides etc. or mixtures thereof are reacted with polyhydroxylated aromatic compounds having two, three, or more hydroxyl groups or mixtures thereof. The only limitation in such variations is that the aromatic PAO ether adducts formed thereby have at least one remaining free hydroxyl group bonded directly to one aromatic moiety in order to effect the subsequent curing reaction with the phenolic aldehyde prepolymer. In all of these embodiments, the compound or mixture of compounds that results from the Williamson ether synthesis steps are referred to herein as "ether adducts."

In somewhat more detail regarding the ether adducts, it is important to adjust the stoichiometric ratio of alkyl bromide moieties to aromatic hydroxyl moieties such that there is at least one hydroxyl moiety remaining on at least one polyhydroxylated aromatic compound incorporated within the ether adduct. In some embodiments, the stoichiometric ratio of alkyl bromide moieties to aromatic hydroxyl moieties is adjusted to provide one hydroxyl group per ether adduct; for example, the exemplary Williamson ether synthesis scheme shown above employs a 1:1 hydroxyl:ether adduct stoichiometric ratio. In other embodiments where one of the more complicated reaction schemes described above is employed—for example, where a PAO dibromide is reacted with two polyhydroxylated aromatic compounds, more than two hydroxyls are present on the polyhydroxylated aromatic compound, etc.—the hydroxyl:ether adduct stoichiometric ratio is selected to be less than one or greater than one. In all such embodiments, the stoichiometric ratio is advantageously selected to optimize the final composition for a particular application or for compatibility in a particular environment.

Further, in some embodiments, it is advantageous to employ an excess molar amount of the polyhydroxylated aromatic compound to PAO in order to ensure that the monoether adduct is favored when carrying out the ether formation reaction. This is particularly true where the polyhydroxylated aromatic compound has two hydroxyl groups; any difunctional ether moieties that form will greatly reduce the reactivity of the adduct to the subsequent reaction wherein the adduct is reacted with the phenolic aldehyde prepolymer to provide the cured compositions of the invention. Thus, in some embodiments where the polyhydroxylated aromatic compound employed to form the ether adduct has two hydroxyl groups, the molar ratio of polyhydroxylated aromatic compound to PAO employed in the ether adduct forming reaction is greater than 1:1, for example about 1.1:1 to 10:1, or about 2:1 to 5:1. In some such embodiments, the unreacted polyhydroxylated aromatic compound is subsequently separated from the ether adduct; in other embodiments, the blend of unreacted polyhydroxylated aromatic compound and ether adduct is employed as-is and blended with the phenolic aldehyde prepolymer. The unreacted polyhydroxylated aromatic compound is reactive with the phenolic aldehyde prepolymer when employed to form the final product.

Epoxy functional PAOs are also useful intermediates by which the aromatic PAO ether adducts are formed. An epoxy PAO is formed, for example, by the reaction of an hydroxyl-terminated PAO with epichlorohydrin in a two step reaction:

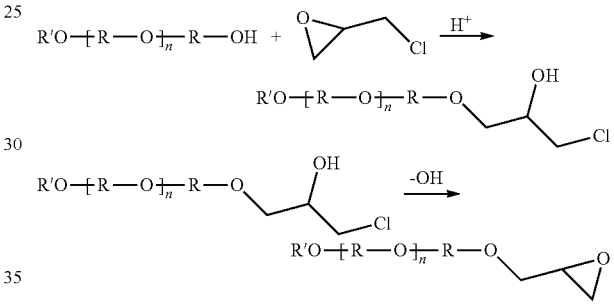

Such a reaction can be accomplished, for example, employing the procedures outlined in Andrews, et al., U.S. Pat. No. 5,420,312 or other conventional literature procedures. Another type of epoxy PAO is formed, in embodiments, by reacting one equivalent of a hydroxyl terminated PAO monoether with one equivalent of a diglycidyl or diepoxy compound in a manner that causes substantially one epoxy moiety to react with one PAO moiety, leaving the second epoxy moiety available for the subsequent reaction. The epoxy PAOs are then employed in a reaction with a polyhydroxylated aromatic compound, using conventional procedures that typically employ protic acid catalysis, to yield the corresponding aromatic PAO ether adduct.

It will be appreciated that several variations of the epoxy PAO intermediate synthesis and subsequent ether adduct formation are selected in various embodiments in order to optimize the final composition for a particular application. Many variations, analogous to the variations on the PAO bromide/Williamson ether synthesis variations described above, are employed in suitable embodiments to optimize the composition. So, for example, epoxidization and ether formation are envisioned employing a difunctional PAO starting material; other variations are envisioned and lie within the scope of the invention.

In each such embodiment, reaction of an hydroxyl-terminated PAO is carried out with the purpose of imparting a PAO terminal group that is either reactive with a selected polyhydroxylated aromatic compound to form an aromatic PAO ether adduct, or is a suitable leaving group in a reaction with a selected polyhydroxylated aromatic compound to form an aromatic PAO ether adduct. Williamson ether synthesis imparts bromide as a leaving group, while the epichlorohydrin addition imparts a reactive epoxy group. Examples of additional suitable leaving groups include, for example, tosylate, brosylate, nosylate, triflate, and mesylate. Others will be envisioned by the skilled artisan.

As in the Williamson ether synthetic pathway, the proviso remains that the aromatic PAO ether adducts formed thereby have at least one remaining free hydroxyl group bonded directly to one aromatic moiety in order to effect the subsequent curing reaction with the phenolic aldehyde prepolymer. In all such embodiments, the compound or mixture of compounds that results from the epoxy PAO synthesis and subsequent reaction with a polyhydroxylated aromatic compound are also referred to herein as "ether adducts."

In some embodiments, the aromatic PAO ether adduct is formed in a protic solvent, such as water or an alcohol. In other embodiments, the aromatic PAO ether adduct is formed in the melt, using no solvent. In still other embodiments, the aromatic PAO ether adduct is formed using an aprotic solvent to facilitate the reaction. Aprotic solvents are usefully employed, for example, to facilitate the reaction to form the aromatic PAO ether adduct while avoiding hydrolysis or alcoholysis, for example, or a leaving group or reaction with a reactive group. Similarly, 100% solids reactions are employed in some embodiments to form the aromatic PAO ether adduct without side reactions attributable to interaction of the solvent with a leaving group or reactive group on the PAO terminus. Illustrative examples of useful aprotic solvents include ethers such as dialkyl ethers, dimethoxyethane, diglyme, and higher dialkyl ethylene glycol ethers, dialkyl propylene glycol ethers, and cyclic ethers such as tetrahydrofuran; dimethyl formamide, dimethyl sulfoxide, esters such as ethyl acetate; and ketones such as acetone and methyl ethyl ketone. Preferably, the aprotic solvent is water soluble and/or able to evaporate under conditions subsequently employed in the synthesis of the cured compositions or composite compositions of the invention.

In one alternative composition, a polyhydroxylated aromatic compound is pre-reacted with a methylolated dialkyl diphenol, such as the methylolated dialkyl diphenols described in Elliott, U.S. Pat. No. 6,811,703. The reaction product thereof is then reacted with the functionalized PAO as described herein. The resulting diphenol-functional ether adducts are capable of participating in crosslinking and bonding reactions with phenolic aldehyde prepolymers in the same fashion as the above described ether adducts. Without wishing to be limited by theory, we believe that the methylolated dialkyl diphenols can act as a source of formaldehyde for the added polyhydroxylated aromatic compounds, thus consuming the reactive methylol groups in a rapid reaction that is similar in nature to the reaction that occurs when the polyhydroxylated aromatic compounds are reacted with a phenolic aldehyde prepolymer. This prevents further cross linking of the methylolated dialkyl diphenols until such time as the phenolic aldehyde prepolymer is added.

This alternative composition has at least two distinct advantages. First, upon subsequent reaction of the methylolated dialkyl diphenol—polyhydroxylated aromatic adducts ("adducts") with the PAO bromide or epoxide, there are multiple hydroxyl groups, for example between 2 and 100, or for example between 3 and 10 hydroxyl groups on each adduct. This is advantageous with respect to ensuring that the adducts—and thus the PAO—are fully reacted and bonded within the crosslinked matrix when the phenolic aldehyde prepolymer is introduced. Second, the pre-reacted adduct ensures that no free diphenol or free polyhydroxylated aromatic compounds are present after the compositions of the invention are fully crosslinked. Because some diphenols and polyhydroxylated aromatic compounds are of concern in the environment, or are volatile at manufacturing or use temperatures, or both, it is an advantage to avoid the possibility of unreacted residues arising from the syntheses employed in conjunction with the cured compositions of the invention.

Other synthetic pathways to form adducts of polyhydroxylated aromatic compounds and PAOs will be easily envisioned. However, preferred reaction pathways will avoid the formation of electron-withdrawing moieties bonded to one or more oxygens of the polyhydroxylated aromatic moieties. Electron-withdrawing moieties tend to reduce the reactivity of the remaining free hydroxyl group(s) present on the aromatic moiety toward the curing conditions and reactions necessary to incorporate the PAO into the phenolic aldehyde network. In part for this reason, reaction pathways resulting in ether formation are electronically favorable for the curing step where the PAO is bonded into the phenolic aldehyde network.

In the various available synthetic pathways employed to form the ether adducts, it is of critical importance for many end uses thereof that a high degree of reaction is achieved, that is, it is important to minimize the residual amount of unreacted, and thereby untethered, PAO at the end of the ether adduct reaction. This is because in certain end uses, such as soil remediation or certain medical uses, untethered PAO will tend to leach out of the cured compositions described below when in the presence of water encountered during use. This in turn leads to loss of the ability of the cured composition to sequester certain chemicals, or provide slow release thereof. Thus, in embodiments, a selected ether adduct forming reaction will achieve at least 75 mol % yield of ether adduct based on the starting amount of PAO. In some embodiments, one or more selected reactive pathways result in between about 75 mol % and 100 mol % formation of ether adduct based on the starting amount of PAO, where 100 mol % reaction means that no unreacted PAO is detectable in the final reaction product using any commonly employed means of detection, including but not limited to $H^1$ NMR, $C^{12}$ NMR, liquid chromatography, gel permeation chromatography, or another means of detection commonly employed by those of skill. In embodiments, the Williamson ether synthesis results in about 90 mol % to 100 mol % formation of ether adduct based on the starting amount of PAO, or about 95 mol % to 99.9 mol % formation of ether adduct based on the starting amount of PAO, or about 97 mol % to 99 mol % formation of ether adduct based on the starting amount of PAO.

4. Phenolic-Aldehyde Prepolymers

Another reagent employed in the reactions leading to the products of the invention is a phenolic-aldehyde prepolymer ("prepolymer"). The phenolic component of the prepolymer includes phenol and various phenol adducts, including bisphenols, as well as polyhydroxylated aromatic compounds such as any of those described above. In some embodiments the prepolymer is a phenol-formaldehyde prepolymer or a resorcinol-formaldehyde prepolymer, or a mixed phenol/resorcinol-formaldehyde prepolymer. In embodiments, the prepolymer is a commercially available waterbased dispersion including the partial reaction product of a hydroxylated and/or polyhydroxylated aromatic compound and an aldehyde. In some embodiments, suitable commercially available prepolymers are in a dispersed form wherein the phenolic and aldehyde have undergone some amount of a characteristic condensation reaction, but curing is not complete. In such form, the prepolymer is relatively stable in the water dispersion. Since formaldehyde exists predominantly in solution as a dynamic equilibrium of methylene glycol oligomers, the concentration of the reactive form of any "free" formaldehyde residing in the prepolymer formulation depends on temperature and pH. Suitable commercially available phenolic aldehyde prepolymers include novalacs, resoles, and blends thereof. In embodiments, a mixture of novalac and resole type dispersions are employed; in other embodiments, a resole type dispersion is employed alone.

Novalacs are available commercially or as prepared in prepolymer dispersions wherein the molar ratio of aldehyde to hydroxylated aromatic compound is less than one, and wherein curing is accomplished using acid or base catalysis, in some embodiments employing heat, along with the addition of an aldehyde or a formaldehyde donor such as hexamethylene tetramine. Examples of suitable novalac cure catalysts include oxalic acid, hydrochloride acid, and sulfonic acid. The prepolymer units are mainly linked by methylene and/or ether groups through the methylolation of the hydroxylated aromatic compound by the reactive form of the aldehyde.

Resoles are phenolic aldehyde resins, similarly available commercially or as prepared in phenolic aldehyde prepolymer dispersions, and having an aldehyde to hydroxylated aromatic compound ratio of greater than one (in embodiments around 1.5). The dispersions are cured after drying using heat and a base catalyst. Phenol, formaldehyde, water and catalyst are mixed in the desired amount and heated, for example to between about 50° C. and 100° C. or between about 60° C. and 80° C. to form a prepolymerized dispersion. The prepolymers will crosslink, in embodiments upon heating to around 120° C., to form methylene and dibenzyl ether bridges via elimination of both the water of dispersion and the water formed by the polycondensation reaction. The result is a stable, three-dimensional cured network. The final crosslinking step gives this type of phenolic resin its characteristic hardness, good thermal stability, and chemical imperviousness.

Resorcinol resins, or resorcinol-phenol resins, are similar to phenol formaldehyde resins except that resorcinol (benzene-1,3-diol) is employed in place of, or in combination with, phenol. In embodiments, phenol and resorcinol based resins are employed in conjunction with the compositions of the invention. Where the recitation herein refers to phenolic aldehyde prepolymers, dispersions, crosslinked compositions, etc. it will be understood that resorcinol or resorcinol-phenol type resins are additionally referred to and included.

Other phenolic aldehyde prepolymers are within the scope of the invention and are useful in conjunction with the ether adducts described above to form the compositions of the invention. For example, in some embodiments lignin adducts or other aromatic hydroxylated compounds are useful alone or in mixtures with phenol, resorcinol, or mixtures thereof or as a replacement for phenol or resorcinol in a prepolymer along with formaldehyde. In some embodiments, an aldehyde other than formaldehyde is useful in the phenolic aldehyde prepolymers. For example, acetaldehyde, propionaldehyde, furfuraldehyde, or another aldehyde or mixture of one or more such aldehydes is useful alone or in a mixture with formaldehyde in the phenolic aldehyde prepolymers. It will be understood by one of skill that the term "phenolic aldehyde" means all of these embodiments and combinations thereof.

Examples of suitable waterbased phenolic aldehyde dispersions that are useful in forming the compositions of the invention include those available from Momentive™ Performance Materials, LLC of Columbus, Ohio under the trade names CELLOBOND® and CASCOPHEN®. Examples of such dispersions include CASCOPHEN® OS 707M, CASCOPHEN® ECO LPF 52, CASCOPHEN® LPF 55, CASCOPHEN® RS 254A and CASCOPHEN® 254D. Another useful dispersion is BINDEX® Resin 73, available from the Indspec Chemical Corporation of Petrolia, Pa. Other suitable dispersions are available from the Georgia-Pacific Corporation of Atlanta, Ga. and the Plastics Engineering Company, Inc. ("Plenco") of Sheboygan, Wis. In embodiments, suitable waterbased phenolic aldehyde dispersions that are useful in forming the compositions of the invention are between about 40 wgt % and 65 wgt % solids, for example about 45 wgt % to 60 wgt % solids. In some embodiments, suitable waterbased phenolic aldehyde dispersions that are useful in forming the compositions of the invention have viscosity of about 50 cP to 500 cP, or about 75 cP to 300 cP; however, for other applications it may be advantageous to employ a dispersion of higher or lower viscosity, depending on the selected manufacturing method. While the pH of the dispersions differs depending on the type of prepolymer and cure catalyst employed, in some embodiments the pH of the dispersion is between 8 and 11 or between 9 and 11.

In some embodiments, depending on the end use intended, a high solids or even a melt-processable phenolic aldehyde resin is useful, wherein the percent solids is, in some embodiments, between 65 wgt % and 100 wgt %. The viscosity of high solids dispersions is, in some embodiments, in excess of 500 cP, for example 10 poise to 10,000 poise or more. Melt processable compositions (essentially 100% solids) have viscosities that depend on the prepolymer molecular weight and processing temperature employed. The compositions of the invention are not particularly limited by the percent solids, viscosity, or molecular weight of the phenolic aldehyde prepolymers employed therein.

In some embodiments, one or more fillers or adjuvant materials are further included in the commercial phenolic aldehyde prepolymer dispersions. For example, wood flour, minerals or glass materials, glass fibers, thermoplastic fibers such as nylon or polyester fibers, or other materials are present in some useful commercial phenolic aldehyde resins. In some embodiments, as is described more fully below, one or more ion exchange entities are added to the reactive composition prior to drying and heating, wherein the cured compositions become adhesively bonded to the ion exchange entities and provide unique performance attributes for water remediation applications. In other embodiments, fillers or adjuvants are added to the cured compositions. The fillers and adjuvants are, in some embodiments, reinforcing; that is, they increase the tensile or compressive strength, impact resistance, modulus, or other physical properties of the compositions of the invention when the compositions are in fully cured form.

5. Reactive Compositions

In some embodiments, a resole or resole/novalac prepolymer is admixed with the ether adduct to yield a reactive composition. In forming such reactive compositions, blending ratios of the prepolymers with the ether adducts are dictated by the total percent solids present in the prepolymer dispersion, if a dispersion is employed, and the type and ratio of PAO functionality present in the ether adduct, further in light of the desired amount of PAO functionality for the end use application. Blending in a dispersion format is typically carried out using conventional techniques, such as vortex mixing, shaking, or static mixing. Extrusion mixing is employed in some embodiments for higher viscosity coating compositions or blending of 100% solids compositions. In some embodiments the reactive compositions undergo a minor amount of reaction while in dispersion form, but such reactions do not cause the dispersion to become unstable, fully cure, precipitate, or phase separate. In some embodiments, the reactive compositions contain additional materials such as the fillers and adjuvants described above. In other embodiments, the reactive compositions consist essentially of an ether adduct, a phenolic aldehyde prepolymer, an amount of a cure catalyst, and water.

In embodiments, a desirable ratio of ether adduct to phenolic aldehyde in a reactive composition results in a ratio of theoretical (before any reaction) phenol or resorcinol groups to formaldehyde of 1:1. Under such conditions, the phenolic aldehyde becomes completely cured. This is because one mole of formaldehyde methylolates one mole of phenol, and methylolated phenols self-condense. In this sense, a methylolated phenol can be considered a "reactive hydroxyl" moiety within the system. The ether adducts, when added to the phenolic aldehyde prepolymer dispersion, contribute one or more reactive aromatic loci, in a manner similar to phenols that react with methylolated phenols at the 2- or 4-locus relative to the single hydroxyl moiety present thereon. Without being bound by theory, we believe that the ether adducts form methylene bridges with neighboring methylolated phenols in the cured compositions, as will be appreciated by one of skill in the art of phenolic aldehyde curing mechanisms.

While the ether adducts participate in the curing reaction upon contact with the phenolic aldehyde prepolymer, the inherent difference in reactivity between a methylolated phenol and the activated aromatic loci present on the ether adducts is the key to the shelf stability of the ether adducts. The activated aromatic loci of the ether adducts do not self-condense as do methylolated adducts such as methylolated alkyl diphenols; the ether adducts are therefore shelf-stable for an indefinite period and yet react rapidly when added to a phenolic aldehyde prepolymer. Cure rate of the reactive composition is dependent on temperature. In general, the rate of cure is adjusted according to the means of application of the reactive composition to a substrate and the manufacturing considerations that make crosslinking reaction practicable and result in a product that is useful for the intended end use.

In contrast to the lack of self-condensation reactivity of the ether adducts noted above, when contacted with formaldehyde, phenolic aldehyde prepolymer, or a combination thereof, the ether adducts of the invention are more reactive than their monohydroxylated aromatic relatives. For example, resorcinol reacts with formaldehyde at a rate that is more than 12 times the comparative rate of reaction of formaldehyde with phenol at pH 3.5. (Durairaj, R., *Resorcinol Chemistry, Technology, and Applications,* ©2005, Springer-Verlag Berlin, Heidelberg, at p. 181.) This rate difference is the minimal difference; the reactivity difference increases between pH 3.5 and pH of about 11. The difference is attributable to the enhanced electron density at the benzene ring 2, 4, and 6 positions. Thus, ether adducts having resorcinol as a starting material are more reactive in the reactive compositions than phenol or even phenol derivatives such as m-cresol.

In some embodiments, the ratio of ether adduct to phenolic aldehyde prepolymer employed to form a reactive composition of the invention is adjusted to reflect the intended end use as well as the type and amount of PAO incorporated into the ether adduct. Additionally, as is discussed above, in some embodiments the ether adducts are formed using an excess molar ratio of polyhydroxylated aromatic compound; in such embodiments, if the product ether adduct is not separated from the unreacted polyhydroxylated aromatic compound, the reactive composition is formed using a mixture of the polyhydroxylated aromatic compound and the ether adduct. In such embodiments the ratio of reacted to unreacted polyhydroxylated aromatic compound must be accounted for in formulating the reactive composition.

In some embodiments, the ratio of ether adduct (including the blends of ether adduct and unreacted polyhydroxylated aromatic compound described above) to phenolic aldehyde in the reactive composition is about 5:1 to 1:10 by weight of solids, or about 2:1 to 1:7 by weight of solids, or about 1:1 to 1:5 by weight of solids, or about 1.2:1 to 1:3 by weight of solids. Additional components of a reactive composition include, in some embodiments, formaldehyde, water or an aprotic solvent, and a cure catalyst such as sodium hydroxide, sulfuric acid, or a cure catalyst resin sold by Georgia Pacific Corporation of Atlanta, Ga. under the trade name REST-CAT®, such as GP® 012G23 RESI-CAT®. In some embodiments, additional components are employed; such additional components are typically added in light of a particular end use or end form of the compositions upon curing. For example, one or more colorants, bleaches, surfactants, solvents, fillers, functional compounds, functional materials such as clay or zeolite, antifungal or antibacterial materials, thermal stabilizers, UV stabilizers, and the like are optionally added to the reactive compositions of the invention so as to provide a particular composition upon curing.

In some embodiments, reactive compositions that are dispersions have a total solids content of about 2 to 90 wgt % based on the weight of the dispersion, or about 10 to 80 wgt %, or about 20 to 75 wgt %, or about 25 to 60 wgt % solids based on the weight of the dispersion.

In one embodiment, a surfactant is employed in the reactive compositions of the invention so as to form a stabilized emulsion that remains stable during and after cure. In some embodiments, the amount and type of surfactant employed is optimized for the intended end use and further in light of the critical micelle concentration of the surfactant, size of emulsion particles formed at a particular concentration of surfactant, and the like. In some embodiments, formation of an emulsion is not necessary to stabilize the reactive composition, but rather to maintain emulsion stability during the reaction of the reactive composition, and provide a cured composition (wherein "cured composition" is described in more detail below) that is a stable waterbased emulsion. In some embodiments, the surfactant employed is nonionic. In some embodiments, the surfactant employed is ionic. In some embodiments, a mixture of two or more surfactants and/or surfactant types is employed. In some embodiments, the surfactant is a quaternary amine or ammonium functional surfactant, or a phosphatidyl functional surfactant.

In some embodiments, one or more reactive compounds are added to the reactive composition. The reactive compounds are reactive with the reactive compositions of the invention to become bonded into the cured composition and in some embodiments undergo the bonding reaction during the curing reaction to form the cured composition. In other embodiments the reactive compounds are reacted with the cured composition, or are reacted within and/or on the surface of the cured composition. Such reactive compounds are included in the reactive compositions to add specific functionality to the cured composition. One example of a reactive compound is 3-chloro-2-hydroxypropyltrimethylammonium chloride, sold as a 65 wt % or 69 wt % aqueous solution under the trade name QUAT® 188 by the Dow Chemical Co. of Midland, Mich.; inclusion of this compound in the reactive composition results in formation of cationic functionality within, and in embodiments bonded to, the cured composition. In another embodiment, a primary dibromoalkyl compound is reacted with a ternary amine, a phenol, polyhydroxylated aromatic compound, or ether adduct moiety thus generating a quaternary ammonium compound that is prereacted in a manner that will result in its incorporation into the crosslinked network formed on curing the reactive compositions of the invention. In some embodiments, a surfactant is a reactive compound; in some embodiments, a reactive compound is not itself a surfactant but provides surfactant-like properties once bonded to the cured composition by maintaining the cured composition in an emulsified state after cure. Other chemical functionality is similarly incorporated in the reactive compositions of the invention with ease.

In some embodiments, a reactive composition is formed by adding formaldehyde or another aldehyde alone to an ether adduct; that is, an aldehyde and the ether adduct are reacted without addition of a phenolic aldehyde prepolymer. In such embodiments, the ratio of ether adduct to aldehyde employed to form a reactive composition of the invention is adjusted to reflect the intended end use as well as the type and amount of PAO incorporated into the ether adduct. Additionally, as is discussed above, in some embodiments the ether adducts are formed using an excess molar ratio of polyhydroxylated aromatic compound; in such embodiments, if the product ether adduct is not separated from the unreacted polyhydroxylated aromatic compound, the reactive composition is formed with an aldehyde and a mixture of the polyhydroxylated aromatic compound and the ether adduct. In some embodiments, the ratio of ether adduct (including the blends of ether adduct and unreacted polyhydroxylated aromatic compound described above) to aldehyde in the reactive composition is about 5:1 to 1:3 by weight of solids, or about 3:1 to 1:1 by weight of solids. Additional components of such reactive compositions include a cure catalyst, such as any of those listed above. In some embodiments, additional components such as any of those listed above are also included in the reactive composition; further, one or more surfactants or reactive compounds are suitably employed in the reactive composition as described above to impart selected functionality to the reactive composition formed with an aldehyde, further in the absence of phenolic aldehyde prepolymer.

6. Cured Compositions

The final curing step of the reactive compositions of the invention are carried out using processes and conditions that are conventionally employed to cure commercially available resole type phenolic aldehyde prepolymer dispersions: namely, drying and application of heat; in some embodiments curing includes acidification of the reactive composition. Such conditions are sufficient to cause the ether adducts in the reactive composition to become fully reacted with, and incorporated into, the three-dimensional phenolic aldehyde network thus formed. The cured phenolic aldehyde polymers having ether adducts incorporated and covalently bonded therein are "cured compositions" of the invention.

Without being limited to theory, we believe that the ether adduct (that is, the aromatic PAO ether adduct) does not require methylol groups to participate in crosslinking with the phenolic aldehyde prepolymer. That is, the presence of the methylol groups in the phenol formaldehyde prepolymer is sufficient to cause reactions with the ether adduct, likely at the electronically activated sites on the aromatic ring as discussed above, to yield a crosslinked network. It is generally known, in an analogous example, that di- or trihydroxybenzene has a greater propensity to spontaneously cross link within a methylolated phenolic prepolymer than e.g. a phenol or diphenol compound, wherein only one oxygen atom is bonded to a conjugated aromatic compound. Similarly, other fully conjugated aromatic compounds having two or more hydroxyl groups situated in positions that provide an activating amount of electron density to one or more unsubstituted loci of the aromatic compound are suitably employed in the reactions of the invention and lead to reactive compositions having the characteristics of extended shelf life and no requirement of additional methylol functionality to accomplish the crosslinking reaction. When such compounds further contain PAO substituents, the PAO is thereby incorporated into the cured compositions of the invention.

In some embodiments, a suitable curing process includes lowering the pH by addition of an acid cure catalyst to the reactive composition. In some such embodiments, lowering the pH is accomplished along with heating the reactive composition to affect rapid cure. Useful examples of acid catalysts include any of the known acid catalysts employed to cure conventional phenolic aldehyde polymers, for example sulfuric acid, phosphoric acid, toluenesulfonic acid, phenoldisulfonic acid, phenolsulfonic acid, and cure catalyst resins (solid state acid-functional resins) such as those sold by Georgia Pacific Corporation of Atlanta, Ga. under the trade name RESI-CAT®, such as GP® 012G23 RESI-CAT®. In such embodiments, all the components of the reactive composition must be acid stable; thus, in embodiments where e.g. a surfactant is employed to form an emulsion, the surfactant must be stable to acidic components and at the pH employed to accelerate curing of the reactive composition. The pH of the resulting reactive composition is targeted to be 3 or less, ideally between 3 and less than 1. In some embodiments, a period of acidic pH is followed by neutralization to a pH of over 3, for example between 3 and 11.5, or between 4 and 10 or between 4.5 and 9. Such neutralization minimizes side reactions such as cleavage of the aromatic PAO ether adducts.

In some embodiments, processing of the reactive composition is concomitant with the curing reaction to yield the final cured composition. For example, in some embodiments, coating of the reactive composition onto a substrate, drying the coated substrate, and heating the substrate to a suitable cure temperature results in formation of the cured composition in situ. In some embodiments, drying is accelerated by heating, for example by forcing dry air into and around the substrate and the like. In such curing processes, suitable coating weights will be determined by the percent solids of the reactive composition dispersion and the desired final amount of cured composition when coated on a substrate. In other embodiments, the reactive compositions are cured in an emulsified form prior to application of the cured composition to a film, particle, or other surface.

Depending on the cured vs. reactive nature of the composition, percent solids in water, rate of cure if applicable, intended end use, and substrate employed, the amount of the reactive composition or cured emulsified composition coated vary over a broad range of both wet and dry coated weight. The invention is not particularly limited by the amount of material coated as a weight percent of the substrate onto which the material is coated. However, examples of suitable coating weights of the reactive compositions or the cured emulsified compositions of the invention range from about 0.01 to 100 wgt % of the based on the weight of the substrate, for example about 0.1 to 90 wgt %, or about 0.25 to 80%, or about 0.5 to 60 wgt %, or about 1 to 50 wgt %, or about 5 to 40 wgt %, or about 5 to 30 wgt %, or about 5 to 20 wgt % of the dispersion based on the weight of the substrate. After the compositions are fully cured and dried, a coated substrate typically has about 0.1 to 50 wgt % of the cured composition based on the weight of the uncoated substrate; or about 1 to 40 wgt %, or about 2 to 30 wgt %, or about 2 to 20 wgt % cured composition based on the weight of the uncoated substrate.

In the case of porous or absorptive substrates, in some embodiments a higher amount of both reactive composition and cured emulsified composition can be added compared to nonporous and nonabsorptive substrates. This in turn results in a higher dry weight of cured composition to the substrate. For example, an absorptive substrate such as cotton batting, a superabsorptive polymer, a nonwoven cellulosic substrate, and the like could easily take on about 100 to 1000 wgt % or more of a reactive composition or cured emulsified composition based on the dry weight of the substrate, or about 200 to 700 wgt % or about 300 to 500 wgt % of the reactive composition or cured emulsified composition based on the dry weight of the substrate. Depending on the percent solids in the reactive composition or cured emulsified composition, the added weight percent solids of the dried cured composition on an absorptive or porous substrate is in some embodiments as high as 5 to 500 wgt % solids added to the substrate based on the weight of the uncoated substrate, although less can be added as selected for the intended end use.

Suitable temperatures employed to cure the reactive composition range from about 30° C. to 200° C., or about 50° C. to 175° C., or about 60° C. to 150° C., or about 100° C. to 150° C., or about 125° C. to 150° C. In some embodiments, the reactive compositions are fully cured after about 30 minutes at about 130° C.

In some embodiments, the reactive compositions are fully cured in emulsion form, wherein the cured compositions are stable cured emulsified particles dispersed in water. In some such embodiments, the cured compositions are employed as a spray or a coating that can be applied by brush, roller, die, or other coating means employed to coat conventional emulsion type products. The stabilized emulsions described above are advantageously employed in this manner in some embodiments. In some embodiments, where a surfactant is bonded to the emulsified particles before or during the curing step, stabilized formulations are formed upon cure wherein the surfactant does not later leach out of the emulsion particles. Where the surfactant is a cationic surfactant, for example, the cured compositions with surfactant covalently bonded thereto are useful to e.g. bind to cation exchange sites present on a soil or leaf surface.

In some embodiments, a cationic or anionic functionality that is provided within the cured compositions of the invention impart surfactancy to the composition, even though the ionic moiety itself is not a surfactant. In other words, simply providing ionic functionality to the cured composition causes surfactancy in some embodiments because of the PEG chains also present within the cured composition, or the aromatic functionality present, or both; additional functionality provided to the cured compositions, such as e.g. $C_6$-$C_{24}$ chain alkyl groups as discussed above, are also the source of surfactancy imparted to the cured compositions of the invention.

In some such embodiments the cured composition is employed as a carrier to control the release of an active ingredient and reduce the rate of leaching of the polymeric carrier; in other embodiments the binding ability of the cured composition is useful for keeping the cured composition in its intended location, and/or for increasing compatibility of a compound to be scavenged by the cured compositions. In other embodiments where a surfactant is included with the reactive composition, it is desirable to remove the surfactant after cure, such as by leaching or washing from the cured composition particles, prior to employing the cured composition in its intended application.

In a non-limiting example employing a surfactant, a reactive composition is formed by charging an ether adduct and a phenolic aldehyde prepolymer in water into a high shear mixer. In some embodiments, additional water is added. In some embodiments, a reactive surfactant was previously added to the prepolymer; in other embodiments, the surfactant is added under high shear to facilitate the formation of micelles. Under high shear mixing the pH is gradually lowered by the addition of an acid. Shear is maintained for time sufficient to complete the polymerization and crosslinking of the micelles. In some cases, the temperature of the dispersion or emulsion is raised to increase the rate of polymerization and cure. In some cases, the final product is filtered to remove oversize coagulum.

In some embodiments, the cured compositions are formed by the reaction of one or more ether adducts and one or more aldehydes, without the inclusion of a phenolic aldehyde prepolymer. In such reactive compositions, the ether adduct or mixture thereof reacts with the aldehyde or mixture thereof directly in a polycondensation reaction catalyzed by acid, base, and/or heat to result in a cured composition. For example, the initial reaction of an ether adduct with formaldehyde forms methylol groups on the one or more ether adducts in the reactive composition. The alkylol groups self-condense under reactive conditions to form a cured composition that is a gel-like material. Resorcinol-formaldehyde aerogels were previously reported by Pekala, R. W., J. Mat. Sci. 24 (1989) 3221-3227. The gels of the invention include PAO functionality covalently bound within the gel network. Such gels include, in embodiments, PAO content of 50% by weight of solids or more, for example about 50 wt % to 98 wt % PAO based on total solids; or about 75 wt % to 96 wt % PAO based on total solids, or about 90 wt % to 95 wt % PAO based on total solids of the gel. In an additional related embodiment, an additional amount of one or more polyhydroxylated aromatic compounds or additional aromatic compounds are added to the reactive composition and thus incorporated into the cured compositions of the invention. In some such embodiments, the additional amount of one or more polyhydroxylated aromatic compounds or additional aromatic compounds is a compound that includes surfactant-like properties or imparts surfactant-like properties to the cured composition. In one such representative example, sodium phenoldisulfonate is the additional aromatic compound. In still another related embodiment, one or more surfactants are incorporated into the reactive composition and thus are physically entrained in the gel.

In an embodiment, the gel-like cured compositions are further processed after formation. In some such embodiments, the gel-like cured compositions are mechanically disrupted by high shear mixing, for example by a homogenizer, an ultrasound device, or some other mixing device that breaks the gel-like material into colloid-like particulate dispersions in water.

In some embodiments, the gel-like cured compositions or the colloid-like particulates are further functionalized to impart a targeted zeta potential to the particle surfaces. For example, in some embodiments, one or more reactive compounds are added to the gel-like cured composition either before or after mechanical disruption, wherein the reactive compounds become covalently bound to the cured gel-like composition or the colloid-like particulate through reaction with hydroxyl groups residing on the aromatic moieties of the cured composition. One example of a reactive compound is 3-chloro-2-hydroxypropyltrimethylammonium chloride, sold as a 65 wt % or 69 wt % aqueous solution under the trade name QUAT® 188 by the Dow Chemical Co. of Midland, Mich.; addition of this compound to the cured gel-like composition, or the colloid-like particulate, results in formation of cationic functionality bonded to the cured composition due to reactivity of residual nucleophilically activated sites present in the polyhydroxylated aromatic functionality within the cured composition.

Using similar techniques, other chemical functionalities are easily envisioned as being incorporated within and bonded to the cured gel-like compositions or colloid-like particulates of the invention with ease by employing other reactive compounds. In some embodiments, it is advantageous to add the selected reactive compound to the cured composition rather than the reactive composition, for example where the reactivity of a polyhydroxylated aromatic ring towards cure is decreased by the presence of the selected functionality once bonded to the polyhydroxylated aromatic ring.

7. Composite Compositions

In some embodiments of the invention, cured compositions employed as water remediation compositions, water retention compositions, controlled release compositions, and the like are one element of a composite composition, wherein the properties of the cured composition works in conjunction with other elements in a composite composition to achieve the remediation or release performance. The other elements of the composite composition are, in various embodiments, one or more compounds, polymers, particles, substrates including films, fibers, adjuvants, fillers, and combinations of two or more thereof. The elements are used in conjunction with the composite, for example, by blending an element with the reactive composition prior to cure, by having the reactive composition coated and cured on the element, by mixing or blending the element with the cured composition, by coating the element onto the cured composition, by coating or adhering the element onto the reactive composition which in turn is coated onto another element, by having the cured composition disposed within the element, by having the cured composition distributed or dispersed throughout the element, or any number of other useful formats. The composite compositions of the invention are not particularly limited as to the additional elements combined therewith, nor by the particular format employed in use thereof.

In embodiments, the composite composition is a cured composition coated over at least part of the available surface of sand particles. Sand of varying grit size is a natural product that provides a useful amount of surface area for applications such as water remediation, does not soften or degrade during the curing process, and adheres strongly to the cured compositions after coating and curing. The reactive compositions are applied by conventional spray or immersion coating, followed in some embodiments by a simple curing process.

In one such embodiment, the composite composition is a cured composition coated over at least part of the available surface of sand particles, wherein the cured composition further has additional particles adhered thereto. In such embodiments, reactive compositions are coated onto the sand and then coated with one or more additional particulates such as clay, metal oxides, zeolites, or synthetic ion exchange materials. The composite is heated sufficiently to form the cured composition. We have found that using this technique, the cured composition adheres strongly to the additional particulates as well as to the sand, forming a stable composite composition. In this manner, additional desirable properties are imparted to the composite compositions of the invention. For example, in embodiments where the additional particulate is clay, the natural ion exchange capacity of the clay is imparted, providing the ability of the composite composition to adsorb e.g. organic and ionic compounds from water sources; further, the clay coating does not swell sufficiently to prevent water flow through media such as soil, making such composite compositions ideal as water remediation compositions in many applications. Additionally, the nature of the ionic environment, in conjunction with the tethered PAO chains present in the cured composition, together define a biphasic system that in turn affects the fate of an adsorbed species.

While clay coated sand is known in the art, it is used primarily for cosmetic reasons or to avoid certain problems associated with using pure clay in certain applications. These problems include dust, reduced water percolation, and the production of a slimy surface when wet. For example, U.S. Pat. Nos. 5,583,165 and 6,048,377 to Kviesitis teach the use of a polymer, e.g. polyvinyl alcohols to glue clay to sand. The final product is a clay coated and with a "clay color". This product retains none of the clay's ion exchange capacity nor the water holding capacity and thus would be of little benefit to a soil profile via the clay's (or other particles) water holding or catalytic capability, or ion exchange capacity.

In some embodiments, after sand particles are coated with the reactive composition, about 2-20% by weight, for example about 7-13% by weight, or about 10% by weight, of finely divided clay, colloidal or agglomerated silica, zeolites, nanoporous, mesoporous, or another porous charcoal (carbon), oxides or hydroxides of calcium, aluminum, or silicon, or a transition metal compound or catalyst including oxides, hydroxides, and organometallic derivatives of manganese, iron, titanium aluminum, calcium, vanadium, chromium, tantalum, tungsten, palladium, platinum, silver, gold, copper, nickel, zinc, or a combination or mixture of two or more of these is slowly added to the sand with accompanying agitation. In some embodiments, the incorporation of ferromagnetic domains is accomplished by including particles of iron II oxide, iron III oxide, nickel oxide, cobalt oxide, mixtures thereof, magnetic rare earth mixtures, and the like. The finely divided materials can be microparticles or nanoparticles in addition to standard mesh particles. When all the finely divided material is sorbed onto the sand, the sand product is heated to about $100°$-$220°$ C., for example about $150°$ C. for about 10-120 minutes, for example about 45 minutes, to effect polycondensation and crosslinking. The resulting composite composition is pH adjusted with acid (e.g. hydrochloric, acetic, sulfuric, etc.) to a pH of about 4-8, for example about 6, and washed free of fines. Alternatively, the final polymerization can be acid catalyzed, thereby eliminating the need for a high cure temperature, but in some embodiments acid catalysis is deleterious to the one or more other materials employed to form the composite composition. Thus, the use of either higher temperatures or acid catalysis to effect condensation will be selected by one of skill depending on the other elements of the composite composition that are present at the time of cure.

In some embodiments, particulates other than sand are advantageously employed in a composite composition. Microparticles and nanoparticles of clay, colloidal or agglomerated silica, zeolites, nanoporous, mesoporous, or another porous charcoal (carbon), oxides or hydroxides of calcium, aluminum, or silicon, or a transition metal compound or catalyst including oxides, hydroxides, and organometallic derivatives of manganese, iron, titanium aluminum, calcium, vanadium, chromium, tantalum, tungsten, palladium, platinum, silver, gold, copper, nickel, zinc, or a combination or mixture of two or more of these, and the like are employed in some embodiments as a substrate upon which the cured compositions are disposed, for example by coating a reactive composition on the substrate followed by curing. In other embodiments, the particulates are admixed with the reactive compositions and the materials are cured in contact with one another. The composite compositions of the invention are not particularly limited as to the size of the one or more particulates, or substrates, included within, disposed underneath, or disposed on the cured compositions.

C. Water Remediation Compositions and Applications Thereof

The cured compositions of the invention, and composite compositions including the cured compositions, are useful in various forms and embodiments as water remediation compositions. In such applications, a reactive composition selected for type and ratio of phenolic aldehyde prepolymer and ether adduct is applied to a surface by coating or spraying and subsequently cured to form a useful water remediation composition. Optionally one or more additional materials are added to the reactive composition prior to curing.

In some embodiments, the surface to which the reactive composition is applied is a part of the water remediation environment itself. In other embodiments, the surface is a temporary carrier, such as a belt or drum, where the reactive composition is dried and cured; and the cured composition is collected after cure and applied to the water remediation environment, optionally after blending with one or more other suitable materials. In still other embodiments, the surface to which the reactive composition is applied is a carrier surface intended to deliver the cured composition as a composite composition, along with other elements optionally included in the composite, to the remediation environment and secure it therein.

Some water remediation embodiments are described herein below; it will be appreciated that other such applications are easily envisioned and lie within the scope of the invention.

1. Soil Remediation and Soil Remediation Environments

In embodiments, a remediation environment wherein the cured compositions of the invention are employed as water remediation compositions is a soil environment. Soil environments include lawns, golf greens, agricultural fields (i.e., gardens, vineyards, pastures, crop fields, fruit or vegetable orchards), nursery potting soil, or any other soil containing location that pesticides or other organic compounds are applied or into which undesirable or excess compounds are leached (i.e., industrial facilities, waste storage or treatment facilities, job sites, construction sites, chemical factories, weapon facilities, etc.). In many embodiments, movement of compounds through soils is facilitated by the movement of water. Amounts of even the most hydrophobic compounds are carried along with water within the soil and delivered to plants, insects, animals, and fresh water sources such as streams, rivers, sedimentation ponds, and lakes. The compounds are then taken up by these entities, wherein even beneficial compounds such as fertilizers cause unintended consequences when present in excess. Excess fertilizer for lawns and crop fields, for example, are known to cause blooms of algae in fresh water when excess amounts are transferred via water in the soil; such blooms, in turn, deplete the freshwater sources of oxygen. Thus, the water remediation compositions of the invention are advantageously placed in soils where undesirable compounds, or harmful amounts of otherwise harmless or beneficial compounds are located. The water remediation compositions of the invention are capable, in various embodiments, of adsorbing excess fertilizers, pesticides, herbicides, or nematicides that otherwise can leach into groundwater and fresh water sources. Additionally, the water remediation compositions of the invention are capable, in various embodiments, of adsorbing undesirable chemicals inadvertently introduced into soils. Such undesirable chemicals include those leaching into the soil from landfills, construction sites, waste containment sites, and the like.

In embodiments, because the cured compositions of the present invention are easily affixed or coated onto a number of substrates of different sizes and material composition prior to use, composite compositions of the invention are usefully employed as water remediation compositions within the soil or similar growth media. When placed strategically in such water remediation environments, the cured compositions adsorb organic compounds carried by water within the soil. Depending on the substrate onto which the cured compositions are coated and other materials added, the composite compositions also affect, in various embodiments, properties of the soil or media such as ionic content, percolativity, consistency, ability to support plant growth, oxygenation, nutrient retention, moisture retention, or combinations of two or more such properties.

In some such embodiments, soil remediation is enabled by employing the following method to form a composite composition that is applied to soil:

a) coating a reactive composition onto sand particles;

b) mixing a quantity of an ion exchange material with the coated sand particles;

c) heating the mixture to a temperature wherein polycondensation of the reactive composition occurs, resulting in a cured composition; and d) adding the cured composition to the soil to be amended.

In embodiments, the composite composition includes clay particles to impart ion exchange capacity, thereby enabling retention of fertilization cations from the water present in the soil. Also, the clay's inherent anion exchange capacity enables the retention of phosphate and silicate. The resulting composite composition reduces leaching of applied fertilizer, keeping nutrients in the root zone and thus preventing environmental contamination. In some embodiments, the composite composition includes iron hydroxide to impart anion exchange capacity.

In embodiments the composite composition facilitates percolation of water by retaining the porosity of the sand. Simply adding pure clay to soil would result in both swelling of the clay and percolation of fine clay particles through the soil, where they tend to agglomerate or otherwise accumulate and subsequently clog pores and channels present in the soil, thereby impeding percolation. In embodiments the composite compositions adhere the clay to the coated sand, preventing clogging of pores and channels, while maintaining the presence of clay in the soil. The presence of the clay attached to the composite compositions enhances the water holding capacity of the soil, which in turn leads to reduced stress of plants grown in the soil when drought conditions arise.

Additionally, we have found that the composite composition is resistant to the formation of hydrophobic surfaces known to arise in uncoated sand, for example when water having a high content of mineral such as calcium salts are contacted therewith. Sand coated with solely the cured composition provides this effect; the effect is not diminished by the presence of clay. Fully wetting out the composite compositions of the invention is advantageous because such intimate contact allows the adsorbing, ion-exchange, and water retention properties of the composite compositions to be fully realized. Additionally, hydrophobic particulates result in irrigation water channeling around affected areas. Turf, trees, crops, and the like within these areas can experience severe water stress.

Methods of introducing the soil remediation compositions of the invention to the soil in effective soil and water remediation environments include top dressing periodically with cured compositions and composite compositions of the present invention as well as backfilling holes which result from conventional aeration activities carried out e.g. in turf or crop field areas. Another method of introducing the water remediation compositions of the invention to the soil in effective soil and water remediation environments utilizes an underground pipe system that collects water at a centralized location. This may be one or more sloping trenches lined with soil-filter fabric and filled with gravel (French drains), or a perforated pipe with the perforations facing the bottom of the trench and connected to a solid drain line provides more efficient draining, or other subterranean drainage systems. In one such embodiment, the water remediation compositions are added to the soil-filter fabric, in another embodiment the water remediation compositions are added to the gravel. In yet another embodiment, the water remediation compositions are one component of a filter through which water or effluent flows, located for example at a centralized location. In some such embodiments, the filter is constructed so that it is easily replaced.

In various embodiments, an underground pipe and/or filter system is used in conjunction with golf courses, sports fields, lawns, agricultural fields, or in any location that pesticides or other organic compounds are applied such as industrial facilities, waste storage and treatment facilities, job sites, construction sites, chemical factories, weapons facilities, and the like.

a. Herbicides

The cured compositions and composite compositions of the invention are useful to bind and prevent the dispersal or leaching of herbicidal compounds from the soil into unintended areas such as freshwater sources, aquifers, and the like. Her-bicidal compounds are primarily used for weed control and many are well known. Herbicides are basically grouped according to their chemical structures, which include but are not limited to triazines such as indazaflam, sold by Bayer AG of Leverkusen, Germany under the trade name SPECTICLE®, as well as phenylureas, carbamates, phenoxyalkanoic acids, aryloxyphenoxypropanoic acids, (phenoxyacids), sulphonylureus, uracils, pyridazines, amides, dinitroanilines, benzonitriles, triazinone, cyclohexanediones, and others (see, e.g. Tekel and Kovacicova, 1993; Tadeo et al., 1996; Gronwald, 1994). Herbicidal compounds commonly used on USGA golf greens provide a representative sampling of herbicides that are commonly employed in non-crop lawns and fields. A listing of such herbicides and their properties can be found listed at the internet address http://www.usga.org/green.

b. Insecticides

The cured compositions and composite compositions of the invention are useful to bind and prevent the dispersal or leaching of insecticidal compounds from the soil into unintended areas such as freshwater sources, aquifers, and the like. Insecticides are used to control insect populations; some work by killing insects and others work to prevent reproduction thereof. Examples of insecticides that are suitably adsorbed by the cured compositions and composite compositions of the invention include Aldicarb, Allethrin, Ambush, Aminocarb, APM, Basudin, Bioallethrin, Bioremethrin, Biphenthrin, Bufencarb, Butacarb, butoxide, Carbanolate, Carbaryl, Carbofuran, Cinerin 1, Cinerin 11, Counter, Cyfluthrin, Cygon, Cyhalothrin, Cymbush, Cypermethrin, Cythion, Dasanit, Decis, Deltamethrin, Diazinon, Dibrom, Dimethoate 480, Dioxacarb, Dipet, Dyfonate, Dylox, Endosulfan, Ethidimuron, Fenpropathrin, Fenvalerate, Flucyrintae, Fluvalinate, Furadan, Guthion, Hopper Stopper, Imidan, Jasmolin 1, Jasmolin 11, Lagon, Lannate, Lorsban, Malathion, Metasystox-R, Methomyl, Methoxychlor, Mexacarbate, Monitor, Ortho, Oxamyl, Parathion, Permethrin, Piperonyl, Pirimor, Pounce, Promecarb, Pyrethrin 1, Pyrethrin 11, Pyrinex, Resmethrin, Ripcord, Sevimol, Sevin, Sniper, Supracide, Tetramethrin, Thimet, Thiodan, and Tralomethrin; also see, e.g. Chen and Wang, 1996; Yang et al., 1996, and http://www.gov.sk.ca/ajfood/cpg/iccont.htm). Insecticidal compounds commonly used on USGA golf greens and their properties are listed at the internet address http://www.usga.org/green/table3.html.

c. Fungicides

The cured compositions and composite compositions of the invention are useful to bind and prevent the dispersal or leaching of fungicidal compounds from the soil into unintended areas such as freshwater sources, aquifers, and the like. Fungicides adsorbed by the cured compositions and composite compositions of the invention include the class Strobilurins, including e.g. azoxystrobin, sold by Syngenta International AG of Basel, Switzerland under the trade name HERITAGE®; pyraclostrobin, sold by BASF® SE of Ludwigshafen am Rhein, Germany under the trade name INSIGNIA®; and trifloxystrobin, sold by Bayer AG of Leverkusen, Germany as a mixture with triadimefon under the trade name TARTAN®. Other fungicides adsorbed by the cured compositions and composite compositions of the invention include Benomyl, Captan, Chlorothalonil, Copper Sulfate, Cyproconazole, Dodine, Flusilazole, Flutolanil (sold by Bayer under the trade name PROSTAR®), Fosetyl-Al, Gallex, Mancozeb, Metalaxyl, Prochloraz, Propiconazole, Tebuconazole, Thiophanate Methyl, Triadimenol, Tridimefon, Triphenyltin hydroxide and Ziram; also see, e.g. Shishkoff, http://www.bonsaiweb.com/forum/articles/arts/fungicide.html; http://cygnus.tamu.edu/Texiab/Nuts/Pecan/pecanf.html; and Hollomon, 1993. Additional, fungicidal compounds, including trade and common names, may be found in Table 2 at the website http://www.missouriedu/-extbsc/turflfundesc.htm. Areas such as agricultural, turf, and sport fields (golf course, tennis lawns, etc.) frequently are treated with substantial amounts of organic fungicides. Fungicidal compounds commonly used on USGA golf greens and their properties are listed at the internet address http://www.usga.org/green/table3/html.

d. Nematicides

The cured compositions and composite compositions of the invention are useful to bind and prevent the dispersal or leaching of nematicidal compounds from the soil into unintended areas such as freshwater sources, aquifers, and the like. Nematicidal compounds are numerous. Nematicides adsorbed by the cured compositions and composite compositions of the invention include those found at http://www.acesag.auburn.edu/depart/ipm/Nematode.htm and http://www.missouri.edu/-extbsc/turfifundesc.htm. Some nematicidal compounds that are commonly used on USGA golf greens and their properties are listed at the internet address http://www.usga.org/green.

Fenamiphos is one such nematicide. It is an anticholinesterase compound (Nemacurg, Bayer Crop Protection, Kansas City, Mo.) widely used for nematode control on soils, and in particular golf course greens and fairways. There are few labeled alternatives to this pesticide. Snyder and Cisar (1993) observed considerable leaching of fenamiphos metabolites (sulfoxides and sulfones) following fenamiphos application to a USGA green. Leaching of the metabolites, and to a lesser extent the parent compound, greatly exceeded that of all other organophosphates examined (Snyder and Cisar, 2001 and 1995; Snyder, Elliott and Cisar, 2001). Because fenamiphos has been observed in nearby waters in or adjacent to golf courses (Swancar, 1996), and because of a highly-publicized fish kill (Zaneski, 1994), regulations have been issued for limiting fenamiphos use on golf courses. The cured compositions and composite compositions of the invention are of particular utility in conjunction with fenamiphos to prevent or greatly reduce leaching of the compound and its metabolites.

e. Plant Hormones

The cured compositions and composite compositions of the invention are useful to bind and prevent the dispersal or leaching of plant hormones, such as plant growth regulating materials, from the soil into unintended areas such as freshwater sources, aquifers, and the like. Plant hormones adsorbed by the cured compositions and composite compositions of the invention include brassinolides, indoleacetic acid, indolebutyric acid, gibberilins, and cytokinins.

f. Additional Agrochemicals

The cured compositions and composite compositions of the invention are also useful to bind and prevent the dispersal or leaching of one or a combination of two or more of the agrochemicals selected from the following nonlimiting list: 3336 PLUS™ (thiophanate-methyl) (obtained from the Cleary Chemical Corporation of Dayton, N.J.); FORE RAIN-SHIELD™ (mancozeb) (obtained from the Dow Chemical Company of Midland, Mich.); BANOL™ (propyl-3(3-dimethylamino) propyl)carbamate hydrochloride (obtained from Bayer AG of Leverkusen, Germany); CHIPCO™ SIGNATURE™ fosetyl aluminum (obtained from Bayer AG); and various agrochemical products sold by Syngenta International AG of Basel, Switzerland under the following trade names: herbicides such as BARRICADE™ 4FL, BARRICADE™ 65WG, DEPARTURE™, FUSILADE™ II Turf and Ornamental, MONUMENT™75WG, PENNANT™ MAGNUM, PRINCEP™ LIQUID, REFUGE™, REWARD™ Landscape and Aquatic, and TENACITY™; fungicides such as BANNER™ MAXX, BANNER™ MAXX II, CONCERT™ II, DACONIL™ ACTION, DACONIL™ ULTREX TURF CARE®, DACONIL™ WEATHER STIK™, DACONIL™ ZN FLOWABLE, HEADWAY™, HEADWAY™ G, HERITAGE™, HERITAGE™ G, HERITAGE™ TL, HURRICANE™, INSTRATAT™, MEDALLION™, MICORA™, PALLADIUM™, RENOWN™, and SUBDUE™ MAXX; insecticides such as AVID™ 0.15 EC, AWARD™, CITATION™, ENDEAVOR™, FLAGSHIP™ 0.22G, FLAGSHIP™ 25WG, MERIDIAN™ 0.33G, MERIDIAN™ 25WG, SCIMITAR™ CS, and SCIMITAR™ GC; and plant growth regulators such as BONZI™, PRIMO™ MAXX, and TRIMMIT™ 2SC. It will be appreciated that this list is not exclusive and other such compounds and in particular agrochemicals not listed herein are also usefully employed in conjunction with the cured compositions of the invention.

2. Wastewater and Related Remediation

In embodiments, a remediation environment wherein the cured compositions or composite compositions of the invention are employed as water remediation compositions is an aqueous solution or dispersion. In embodiments, the cured compositions or composite compositions of the invention are employed as part of a treatment process or facility for aqueous solutions containing or suspected to contain organic compounds and/or ionic moieties e.g., sewage, groundwater, wastewater, leachate, or industrial runoff. In some embodiments, water collected at a common facility is contacted with a cured composition of the present invention to reduce the levels of organic compounds, such as pesticides in the water. Water treatment systems are well known to those of skill in the art and include, but are not limited to, Sequencing Batch Biological Reactor (SBA), continuous activated sludge, trickling filter, aerated lagoon, and anaerobic filter. Such systems, and others, are adapted to treat organic compounds by employing the cured compositions of this invention. Additionally, as is described above, certain composite compositions have further properties, such as ion exchange properties, that are usefully employed in conjunction with water remediation. Such composite compositions are similarly useful in aqueous solution remediation environments.

In some embodiments, the aqueous solution is treated by contacting the water with particles including the water remediation composition in a batch method. In embodiments, such batch methods include:
  a) adding particles including or consisting essentially of a cured composition to an aqueous solution containing, or suspected to contain, one or more organic compounds or microorganisms;
  b) agitating the particles in the aqueous solution for a sufficient period of time to provide for adsorption of at least a portion of the organic compounds, and
  c) separating the particles from the purified aqueous solution.

In some embodiments of the method, the particles are composite particles. In some such embodiments, the composite particles further include clay, and the agitation further provides for ion exchange of ionic moieties present in the aqueous solution. In some embodiments the composite particles include aluminum hydroxide, wherein the resulting zeta potential of the composite particles will remove e.g. viruses. In some embodiments of the method, separation is accomplished by sedimentation, centrifugation, or filtration through a size selective porous membrane, fritted glass filter, paper filter, and the like.

In some embodiments, the aqueous solution is treated by contacting the water with particles including the water remediation composition by flowing through a column including a water remediation composition or by
  a) coating fibers of a nonwoven filter media with the reactive composition;
  b) curing the reactive composition to provide a fibrous composite composition;
  c) placing one or more layers of the fibrous composite composition in a flow pathway for the aqueous solution, and
  d) flowing the aqueous solution through the flow pathway to provide for adsorption of at least a portion of the organic compounds.

In some embodiments of the method, particles or composite particles containing the cured compositions are dispersed within the nonwoven fibers, or sandwiched between filter media layers instead of, or in addition to, coating fiber with the compositions of the invention. In some embodiments, prior to curing the reactive composition, one or more elements are added to the reactive composition; in some such embodiments, the element added is particulate clay. In such embodiments, the aqueous solution contains or is suspected to contain one or more ionic moieties, and flowing the aqueous solution includes adsorption of at least a portion of ionic moieties present in the aqueous solution.

An alternative embodiment includes coating a film or a glass plate with a reactive composition and curing it, optionally including one or more additional elements, and submersing the composite film composition in the aqueous solution.

U.S. Pat. No. 4,511,657 teaches a method of treating chemical wastes using an SBA system comprising activated sludges. In embodiments, the method of the '657 patent employ the cured compositions of the invention, wherein the cured compositions or composite compositions are added to the biological organism containing activated sludge, or utilized in one or more separate tanks comprising activated sludge, or used in lieu of the biological material. The latter obviates the need to maintain the viability of living organisms.

U.S. Pat. No. 5,685,981 teaches a filter system. In various embodiments, filter apparatuses have an intake port, a chamber, and an outlet port. Conventionally, activated carbon is disposed within a filter chamber to adsorb organic compounds. Activated carbons are available in different grades and with different binding activities. However, not all grades perform well in all purposes and effective grades tend to be expensive. Cured compositions and composite compositions of the invention are used, in various embodiments, in the place of or in addition to activated carbon in the chamber of a filter system. In embodiments, the presence of the cured compositions and composite compositions of the invention increase the range of organic compounds adsorbed from an aqueous solution.

U.S. Pat. No. 4,995,969 teaches a biological living-filter system for the treatment of sanitary landfill leachate which includes a treatment basin lined with a water impervious material and filled with an organically enriched treatment medium conducive to maintaining a population of microorganisms. The system also includes leachate tolerant plants growing in the treatment medium. This system, modified to include one or more cured compositions or composite compositions of the invention, increases the range of compounds adsorbed.

Alternatively, one or more cured compositions and composite compositions of the invention are useful in conjunction with in a landfill leachate treatment system similar to that taught by U.S. Pat. No. 4,995,969, in addition to or in lieu of the biological material described therein. Use of one or more cured compositions and composite compositions of the invention in such a manner obviates the need to establish and maintain a living ecosystem.

In a related embodiment, treatment of water phases containing heavy metals or ions thereof is carried out employing the cured compositions and composite compositions of the invention. The partitioning behavior of the PAO component of the cured compositions and composite compositions of the invention is affected in the presence of bases such as NaOH or $(NH_4)_2SO_4$, wherein their presence in the water phase results, in embodiments, in the uptake of heavy metal ions from the aqueous solution. Such uptake is advantageously employed by the cured compositions of the invention, wherein PAO is tethered within the cured network polymer, effectively sequestering such metal atoms and ions within a phase that is easily separated from the water phase. This partitioning behavior is known with respect to PAOs such as polyethylene oxide, as reported e.g. by Rogers et al., *Sep. Sci. and Tech.*, 30(7-9), 1203-1217, 1995. Water phases treatable using the cured compositions and composite compositions of the invention include water entrained in e.g. soil and the like where the water has entrained within it heavy metals or ions thereof. Examples of heavy metal ions usefully sequestered by the cured compositions and composite compositions of the invention include cesium and strontium ions, oxyanions such as technetate, chromate, molybdate, tungstate, and orthovanadate.

Additional lyotropic anions useful in providing an aqueous PAO liquid/liquid biphase form salts with ammonium or alkali metal cations include hydroxide, fluoride, carbonate, silicate, sulfate, phosphate, dihydrogen phosphate, hydrogen phosphate, formate, succinate, acetate, tartrate, citrate, thiocyanate, thiosulfate, fluorosilicate, orthosilicate, hydroxyethane-1,1-diphosphonate (-2, -3, and -4 anion forms), and vinylidene-1,1-diphosphonate (-2, -3, and -4 anion forms).

Without being limited by theory, we believe that the presence of clay provides a colloidal electrolyte that causes biphase formation at the surface of a composite particle.

3. Medical Remediation

In embodiments, the cured compositions and composite compositions of the invention are useful in one or more medical remediation environments wherein the waterbased solutions/dispersions are bodily fluids. Applications such as purification of toxins or other impurities from blood, kidney dialysis, and the like are addressed by employing the cured compositions and composite compositions of the invention. In dialysis and blood purification, for example, filter cartridges that in some embodiments are the same or similar to those described above for water remediation applications are similarly useful herein. Typically, different types of e.g. filter media, cartridge materials, and the like are employed for medical applications. Further, the composite compositions of the invention employ, in embodiments, elements capable of withstanding sterilization; conventional sterilization employs heat and/or steam and pressure, such as in an autoclave; or chemical treatment such as treatments with ethylene oxide, chlorine dioxide, hydrogen peroxide, and the like; or radiation treatments with gamma rays or electron beams.

When used in place of or in addition to conventional medical purification or dialysis materials, the cured compositions and composite compositions of the invention increase or augment the range of compounds advantageously scavenged from bodily fluids. Organic compounds are scavenged by the cured compositions, while composite compositions include, in embodiments, ion exchanging materials or other materials designed to scavenge specific compounds or classes of compounds. Additionally, the cured compositions of the invention facilitate recovery of pertechnate from radiodye waste streams.

4. Personal Care Remediation

In embodiments, the cured compositions and composite compositions of the invention are useful in one or more personal care remediation environments wherein the waterbased solutions/dispersions are excreted bodily fluids. Excreted bodily fluids include urine, pus, blood, menses, mucosal substances, drainage from wounds or surgical incisions, and the like. Such bodily fluids often contain agents that cause odors to arise. Remediation of such fluids is accomplished by scavenging the organic compounds causing odors, or the agents giving rise to the odors, or both from the excreted bodily fluids. Such agents and compounds are addressed by employing the cured compositions and composite compositions of the invention.

Articles conventionally employed to absorb excreted bodily fluids include bandages, diapers, feminine hygiene products, and the like; collectively, these articles are referred to as personal hygiene products. In embodiments, one or more personal hygiene products is modified to include one or more cured compositions and composite compositions of the invention. Many such personal hygiene products employ nonwoven fabrics therein. In some such embodiments, fibers of a nonwoven fabric are coated with the reactive composition, then cured to form a composite composition that is incorporated into a diaper, bandage, and the like. In other such embodiments, one or more particulates are formed from, or with, the cured compositions of the invention and the particulates are entrapped in a nonwoven fabric for the purpose of remediation.

When used in place of or in addition to conventional materials and articles employed for absorption of excreted bodily fluids, the cured compositions and composite compositions of the invention increase or augment the range of compounds advantageously scavenged. Organic compounds are scavenged by the cured compositions, while composite compositions include, in embodiments, ion exchanging materials or other materials designed to scavenge specific compounds or classes of compounds.

D. Controlled Release Compositions and Applications Thereof

In embodiments, the cured compositions and composite compositions of the invention are suitably employed as controlled release compositions. Controlled release compositions are compositions that are pre-loaded with a compound or a mixture of compounds such that, when the loaded controlled release composition is placed in a release environment, it releases the compound or mixture of compounds at a predictable rate that is slower than the simple addition of the same amount of that compound or mixture thereof into the release environment. In embodiments, the controlled release provides a period during which there is a steady state concentration of the compound or mixture thereof in the release environment; in other embodiments, the range of concentration in the release environment varies continuously over time.

In embodiments, a controlled release composition is characterized in that the concentration of the compound or mixture thereof delivered by the release composition into the release environment is, at any given point in time, less than the initial concentration observed in the release environment when the compound or mixture thereof is added to environment in the absence of the controlled release composition. In other embodiments, a controlled release composition is characterized in that the presence of the compound or mixture thereof, delivered by the release composition into the release environment, is detectable for a period of time after the depletion of the compound or mixture thereof after addition to the release environment in the absence of the controlled release composition.

Pre-loading of a cured composition of the invention for use as a controlled release composition is accomplished using any of several available methods. For example, immersion of the cured composition or composite composition into a concentrated solution of the compound to be released is one suitable method for pre-loading the controlled release composition. In some embodiments, rather than a solution of the compound, the neat compound in liquid form is used. In some embodiments, the addition of heat and/or pressure is advantageously employed to accomplish the pre-loading. In other embodiments, the compound to be released is sprayed, in solution or in neat form, onto the cured composition or composite composition wherein the compound is adsorbed; in some such embodiments, heat and/or pressure is also suitably employed. In still other embodiments, the compound is added to the reactive composition and is thus entrained within the crosslinked matrix at the time of curing to form the cured composition or composite composition. In still other embodiments, the compound is applied to an element for forming a composite composition, and the element is added to the reactive composition such that curing results in a composite composition. In still other embodiments, the compound is added in conjunction with a surfactant, wherein the surfactant associates non-covalently with the cured or reactive composition, and the compound is associated non-covalently with the surfactant. Examples of suitable elements for delivering the compound to the reactive composition include clay, activated carbon, porous silica, or some other particle; or a polymer, crown ether, cyclodextrin, or other compound that forms a clathrate or clathrate-like composition with the compound to be released.

The controlled release compositions of the invention are useful as adjuvants or delivery vehicles for the controlled release of organic compounds into environments containing liquid water.

1. Controlled Release of Soil Treatment Agents

The controlled release compositions of the invention are useful as adjuvants or delivery vehicles for the controlled release of soil treatment agents into water containing soil environments. Suitable soil treatment agents including herbicides, organic pesticides (including nematicides, insecticides, fungicides, and microbicides). Such materials are pre-loaded into a cured composition or composite composition of the invention for controlled release upon contacting a lawn, golf green, agricultural field (i.e., garden, vineyard, pasture, crop field, fruit or vegetable orchard), nursery potting soil, and the like.

The ability to coat and cure the reactive compositions of the invention onto inert and/or ecologically harmless substrates, such as sand particles, provides a biocompatible matrix for not only the controlled release of fertilizers or pesticides to a target area without introducing incompatible or unsuitable adjuvants or substrates into the environment, but also provides an easily used form to accomplish the controlled release composition to the release environment. Further, the ability to adhere e.g. clay or another ion exchange composition to such coated sand particles provides the means to enhance cation and anion exchange, and moisture and nutrient retention capacities of the soil without concurrent reduction in percolation rate.

In embodiments, the controlled release compositions of the invention are also useful in this role when employed as soil remediation compositions. That is, instead of pre-loading the controlled release compositions of the invention before addition thereof to a soil environment, such compositions are useful to adsorb and retain excess fertilizers or pesticides when such are applied as-is to a soil environment; the compositions then slowly release these compounds back to the soil. In such embodiments, the cured compositions or composite compositions of the invention prevent leachates from reaching fresh water sources and at the same time provide for the prolonged release of low levels of the compounds into the soil.

The controlled release compositions of the invention are useful to provide for controlled release in soil, when pre-loaded with one or a combination of two or more of the following agrochemicals selected from the following nonlimiting list of compounds: 3336 PLUS™ (thiophanate-methyl) (obtained from the Cleary Chemical Corporation of Dayton, N.J.); FORE RAINSHIELD™ (mancozeb) (obtained from the Dow Chemical Company of Midland, Mich.); BANOL™ (propyl-3(3-dimethylamino) propyl)carbamate hydrochloride (obtained from Bayer AG of Leverkusen, Germany); CHIPCO™ SIGNATURE™ fosetyl aluminum (obtained from Bayer AG); and various agrochemical products sold by Syngenta International AG of Basel, Switzerland under the following trade names: herbicides such as BARRICADE™ 4FL, BARRICADE™ 65WG, DEPARTURE™, FUSILADE™ II Turf and Ornamental, MONUMENT™ 75WG, PENNANT™ MAGNUM, PRINCEP™ LIQUID, REFUGE™, REWARD™ Landscape and Aquatic, and TENACITY™; fungicides such as BANNER™ MAXX, BANNER™ MAXX II, CONCERT™ II, DACONIL™ ACTION, DACONIL™ ULTREX TURF CARE®, DACONIL™ WEATHER STIK™, DACONIL™ ZN FLOWABLE, HEADWAY™, HEADWAY™ G, HERITAGE™, HERITAGE™ G, HERITAGE™ TL, HURRICANE™, INSTRATAT™, MEDALLION™, MICORA™, PALLA- DIUM™, RENOWN™, and SUBDUE™ MAXX; insecticides such as AVID™ 0.15 EC, AWARD™, CITATION™, ENDEAVOR™, FLAGSHIP™ 0.22G, FLAGSHIP™ 25WG, MERIDIAN™ 0.33G, MERIDIAN™ 25WG, SCIMITAR™ CS, and SCIMITAR™ GC; and plant growth regulators such as BONZI™, PRIMO™ MAXX, and TRIMMIT™ 2SC. It will be appreciated that this list is not exclusive and other such compounds and in particular agrochemicals not listed herein are also usefully employed in conjunction with the cured compositions of the invention.

2. Controlled Release of Insecticides and Insect Attractants.

The controlled release compositions of the invention are useful as adjuvants or delivery vehicles for the controlled release of one or more insecticides. As used herein, the term "insecticide" means a compound or mixture of compounds that kills insects, repels insects, or provides some other effect that mitigates harmful effects of insects or otherwise reduces their numbers; or a combination of one or more such effects. Insect attractants include compounds and mixtures thereof to attract insects. In various embodiments, the purpose of attracting insects is to bring them to a specific location or to attract them away from another location. One example of an insect attractant is a pheromone.

One example of an insecticide is a termiticide. Termiticide solutions or emulsions are conventionally applied to soak into the voids in the soil to create a "barrier" that repels termites from e.g. wooden building structures or construction areas prior to pouring of a foundation slab for a new building. Examples of commonly used termiticides include Fipronil, sold by BASF® SE of Ludwigshafen am Rhein, Germany under the name TERMIDOR®, and Imidocloprid, sold by Bayer AG of Leverkusen, Germany under the trade name PREMISE®. Termiticides are conventionally applied in emulsion form with the purpose of adhering the emulsion to organic carbon sources. In such uses, sandy soils provide more complete percolation, but poor bonding (and thus, lower overall efficacy because the termiticide leaches or washes through the soil); and clay-rich soils offer better bonding in some embodiments but provide fewer gaps for the emulsion to penetrate. If the soil is saturated with water, or if it is too cold, is it not practicable to apply the chemical at the required label rate. In embodiments, the controlled release compositions of the invention are employed to provide a means to apply the termiticide in effective amounts to targeted areas that are otherwise not practicable, or to increase the longevity of termiticide treatment of the soil. It will be understood by those of skill that the compositions of the invention are employed, in various embodiments, as applied to the soil prior to application of the termiticide, or as pre-loaded with the termiticide. The pre-loaded composition is more preferred where percolation of the termiticide emulsion or solution is hampered.

3. Controlled Release of Pharmaceuticals

The controlled release compositions of the invention are useful as adjuvants or delivery vehicles for the controlled release of pharmaceutical compounds, that is, drugs or other medicaments, directly into biological systems. For example, adhesive patches are conventionally employed for controlled release of pharmaceutical compounds into a human patient, where such drugs are able to cross the skin barrier (transdermal) or a mucosal barrier (transmucosal) and be absorbed into the bloodstream. In some cases, animals such as livestock are similarly benefitted by the use of such controlled release articles. Transdermal or transmucosal patches containing controlled release compositions of the invention pre-loaded with one or more pharmaceutical compounds are useful for providing controlled release and have the advantages of being easy and inexpensive to manufacture and chemically inert to the body.

Many suitable embodiments of the cured compositions or composite compositions of the invention are envisioned for such uses. For example, in a representative embodiment, a reactive composition is coated onto a section of polyester film, such as a 1"×1" or 2"×2" section, and one or more medicaments added thereto. The reactive composition is cured to yield a composite composition. Then an adhesive is coated either substantially around the edges of the composition, or over the entirety of the composition, and the coated film employed as a transdermal patch. Similarly, nonwoven media or inert particles are coated with the reactive compositions containing one or more pharmaceuticals; similarly, particles are formed that include the cured composition and one or more pharmaceuticals. In other embodiments, the reactive compositions are coated with particulates containing the pharmaceuticals.

Suitable pharmaceuticals employed in conjunction with the controlled release compositions of the invention include nicotine, painkillers, drugs for the treatment of skin conditions such as acne, psoriasis, eczema, and the like, antibiotics, antifungal, or antiviral drugs, insulin-control drugs, weight loss drugs, drugs for the regulation of mental health conditions such as anti-depressants, anti-psychotics, and the like, heart medications for arrhythmia, high blood pressure, and the like, chemotherapy drugs, natural or synthetic steroids or hormones, dietary supplements and "neutraceutical" compounds and mixtures, or other compounds of therapeutic value for the human body and mixtures of two or more thereof.

Using techniques such as those described above, one or more pharmaceuticals are pre-loaded into a cured composition or composite composition of the invention for controlled release upon contact with human or animal skin or mucosal surfaces. The release is via diffusive or microporous flow or a combination thereof depending on the nature of the cured composition and the composite composition in which the cured composition resides.

E. Additional Applications of the Compositions

In some embodiments, the cured compositions of the invention are usefully disposed as coatings on one or more medical device surfaces. In implantable devices, for example, it is known that polyethylene oxide (PEO) and polypropylene oxide (PPO) surfaces are "invisible" to the human body's various biological reaction systems triggered by e.g. protein or cell adhesion or pickup. The cured compositions of the invention can be designed to have a majority weight percent composition of PEO, for example between 50 wt % and 95 wt % PEO, while still retaining a robust level of crosslinking that imparts durability to a coated surface. Adhesion of the cured compositions to metals, ceramics, thermoplastics, or thermosets commonly employed in medical devices is achieved by curing the reactive composition in situ or, in some embodiments, achieved by post-cure functionalization of e.g. gel-like cured compositions as described above. Thus, cured compositions of the invention are formed in situ, in some embodiments, directly on the surface of a medical device such as an artificial bone or bone section or joint, a stent, a valve, and the like to impart durable anti-fouling properties thereto.

In some embodiments, the cured compositions or composite compositions of the invention are useful in scavenging one or more organic components from a gas, such as air, nitrogen, helium, oxygen, and the like. Volatile organic compounds, or VOCs, are often entrained in sources such as industrial exhaust, incinerator facilities, and the like wherein it is desirable to scavenge VOCs in order to improve the quality of air discharged. Industrial manufacturing of purified gases also requires means to scavenge minor or trace amounts of VOCs therefrom. In some such embodiments, the cured compositions or composite compositions of the invention are useful to reduce or remove VOCs, thereby purifying the gas.

Other air purification applications addressed by incorporating the cured compositions or composite compositions of the invention include passive sources of undesirable compounds in locations where air quality is an issue. For example, automobile cabin interiors, where off-gassing of plasticizers or other impurities by plastic components is a recognized problem; similarly, interior living spaces where carpet or rug backings similarly are known to release harmful compounds are a known issue.

In various embodiments, the filtration type embodiments described above include the cured compositions or composite compositions and are employed for the purposes of filtering a gaseous fluid instead of water. In passive sources of VOCs, coatings of the cured compositions on films or sachets included in an automobile interior, coated on particles entrained in a carpet backing or provided as a layer beneath the backing, and the like are useful embodiments employed to reduce or remove harmful or odorous VOCs from breathable air. The configuration, type of cured composition employed, and amount employed will be selected by one of skill to address the particular gas purification application.

The foregoing is applicable to various compositions and articles of the invention disclosure. The following examples and data further exemplify the invention. The invention may be better understood with reference to the following examples. These examples are intended to be representative of specific embodiments of the invention, and are not intended as limiting the scope of the invention.

F. Experimental Section

EXAMPLE 1

Synthesis of the bromide adduct of polyethylene glycol monomethyl ether was carried out by adding 100 parts by weight of MPEG 5000 (polyethylene glycol, 5000 avg. MW, monomethyl ether; obtained from Ineos Oxide of Switzerland) to a reaction vessel, followed by addition of 2 parts by weight of $PBr_3$ (obtained from GFS Chemical Co. Powell, Ohio) and heating the neat mixture for 3 hrs at 70° C. The product thus formed was collected and used without further purification, and is referred to as MPEG-Br in subsequent sections below.

A reaction vessel was charged with 13.26 g BINDEX® 73 (obtained from the Indspec Chemical Corporation of Petrolia, Pa.) and 3.0 g of a 50 wt % solution of NaOH in water; the contents of the vessel were mixed. Then 102 g of MPEG-Br was added in molten form, at about 70° C., slowly over a period of about 15 min. with stirring. The temperature of the mixture reached about 50° C. After an additional 1 hr of stirring, 250 g of CASCOPHEN® M707 (obtained from MOMENTIVE™ Performance Materials, LLC of Columbus, Ohio) was added and thoroughly mixed into the vessel to form a Composition A.

One kilogram of sand meeting the requirements set forth in "USGA Recommendations for a Method of Putting Green Construction" (2004 Revision), U.S. Golf Association Green Section Staff, publication PG 1110 (publication available at http:/www.usga.org/Contentaspx?id-26124) and ASTM tests listed in Appendix I therein, and 10 g of Composition A were combined in a Cleveland-type benchtop muller. The combination was mixed for about 45 seconds. Then 8 g CAS-COPHEN® W3154N (obtained from Momentive™ Performance Materials), 3 g BAYERFERROX® 918LO (obtained from Lanxess AG of Leverkeusen, Germany (moving to Cologne, Germany in 2013)) and 0.4 g phthalocyanine blue was added to the muller and this combination was mixed for about 45 seconds. Then 25 g Composition A was added to the muller and the combination was mixed for about 45 seconds. Then 70 g PANTHERCREEK® 200 bentonite (obtained from the American Colloid Company of Hoffman Estates, IL) was added to the muller and the combination was mixed for about 1 minute to produce a coated sand product.

The coated sand was collected from the muller and heated to 135° C. for about 30 minutes to yield a coated cured sand. The coated cured sand was cooled to room temperature and tested for cation exchange capacity as well as soluble organic carbon.

EXAMPLE 2

In a reaction vessel, 4.6 g Bisphenol A (obtained from the Ashland Chemical Co. of Ashland, Ky.) was mixed with 1.6 g 50% NaOH. Then 4.9 g of a 37% formaldehyde solution and 1 g of deionized water was added to the vessel. The contents of the vessel were heated to 50° C. and stirred for about 30 minutes to form Composition B.

In a separate vessel, 9.5 g BINDEX® 73 (obtained from the Indspec Chemical Corporation of Petrolia, Pa.) was mixed with 4.8 g of a 50 wgt % NaOH solution in water. Composition B was added dropwise into this over about 10 minutes with stirring. This mixture was allowed to react for 30 min with stirring. Then 102 g MPEG-Br was added in molten form, at about 70° C., slowly over a period of about 10 min with stirring and allowed to react with stirring for an additional approximately 30 minutes. Then 250 g CAS-COPHEN® M707 (obtained from MOMENTIVE™ Performance Materials, LLC of Columbus, Ohio) was and thoroughly mixed to yield Composition C.

One kilogram of the same sand as used in Example 1 and 10 g Composition C were combined in a Cleveland type benchtop muller. The combination was mixed for about 45 seconds. Then 8 g CASCOPHEN® W3154N (obtained from Momentive™ Performance Materials), 3 g BAYERFERROX® 918LO (obtained from Lanxess AG of Leverkeusen, Germany (moving to Cologne, Germany in 2013)) and 0.4 g phthalocyanine blue was added to the muller and this combination was mixed for about 45 seconds. Then 28 g of Composition C was added to muller and the combination was mixed for about 45 seconds. Then 70 g PANTHERCREEK® 200 bentonite (obtained from the American Colloid Company of Hoffman Estates, IL) was added to the muller and this combination was mixed for about 1 minute to produce a coated sand product.

The coated sand was collected and heated to 135° C. for about 30 minutes to yield a coated cured sand. The coated cured sand was cooled to room temperature and tested for cation exchange capacity as well as soluble organic carbon.

EXAMPLE 3

In a reaction vessel, 8.8 g resorcinol (obtained from Dynea USA, Inc. of Toledo, Ohio) was dissolved in 8 g of a 50 wgt % solution of NaOH in water. Then 102 g MPEG-Br was added in molten form, at about 70° C., slowly over a period of about 15 min with stirring. The resulting mixture was stirred for an additional approximately 30 minutes. Then 250 g CAS-COPHEN® OS M707 (obtained from MOMENTIVE™ Performance Materials, LLC of Columbus, Ohio) was added to the vessel with thorough mixing to yield Composition D.

One kilogram of the same sand as used in Example 1 and 10 g Composition D were combined in a Cleveland-type benchtop muller. The combination was mixed for about 45 seconds. Then 8 g CASCOPHEN® W3154N (obtained from MOMENTIVE™ Performance Materials), 3 g BAYERFERROX® 918LO (obtained from Lanxess AG of Cologne, Germany) and 0.4 g phthalocyanine blue were added to the muller and the combination was mixed for about 45 seconds. Then 26 g of Composition D was added to the muller and the combination was mixed for about 45 seconds. Then 70 g PANTHERCREEK® 200 bentonite (obtained from the American Colloid Company of Hoffman Estates, IL) was added to the muller and the combination mixed for about 1 minute to produce a coated sand product.

The coated sand was collected and heated to 135° C. for about 30 minutes to yield a coated cured sand. The coated cured sand was cooled to room temperature and tested for cation exchange capacity as well as soluble organic carbon. Two drops of 0.5 wt % Methylene Blue dye in water was added to an aliquot of the coated sand in water and the slurry was shaken briefly then allowed to stand for several minutes followed by decanting the water from the sand; the sand was washed with clean water. The washed sand exhibited a purple sheen, characteristic of the association of the dye with the cation exchange sites of the clay.

EXAMPLE 4

In a reaction vessel, 100 g resorcinol (obtained from the Indspec Chemical Corporation of Petrolia, Pa.) was dissolved in 100 g of deionized water. Then 2 g of oxalic acid was dissolved in the resorcinol solution and the mixture was brought to reflux. Then 50 g of a solution of 37% formaldehyde in water was added slowly to the refluxing mixture with vigorous stirring. After the addition was completed the mixture was allowed to stir under reflux conditions for about 1 hour to yield Composition E.

Composition E is used, in conjunction with one or more brominated alkylene oxide compounds and one or more phenolic aldehyde or resorcinol prepolymers, to form coated cured sand products using the general techniques outlined in Examples 1-3 above.

EXAMPLE 5

A 1 L Erlenmeyer flask was charged with 25.3 g deionized water and 12.65 g BINDEX® 73 (obtained from the Indspec Chemical Corporation of Petrolia, Pa.). The mixture in the flask was sparged with Argon gas. Then 6.4 g of a 50 w/w % solution of sodium hydroxide was added to the flask and the mixture and stirred until it appeared homogeneous. Then 100 g MPEG 5000 Br was added slowly to the flask with vigorous mixing, over about 30 minutes; stirring was continued for an additional period of about 45 minutes. Then 356 g of CASCOPHEN® OS 707M (obtained from MOMENTIVE™ Performance Materials, LLC of Columbus, Ohio) was then added to the flask with vigorous agitation.

About 25 g of this mixture was removed from the flask and added to 900 g silica sand in a Cleveland-type laboratory benchtop muller and the combination was thoroughly mixed. Then 8 g CASCOPHEN® W3154N-1 (obtained from MOMENTIVE™ Performance Materials), 0.3 g phthalocyanine blue and 3 g BAYERFERROX® 91LO Yellow (obtained from Lanxess AG of Cologne, Germany) were added to the muller and this combination was mixed for about 1 minute.

Then 70 g of PANTHER CREEK® 200 Calcium Bentonite (obtained from the American Colloid Company of Hoffman Estates, IL) was added to the muller and this combination was mixed for about 1 minute to result in a coated sand product. The coated sand product was removed from the muller and placed in an oven set at 150° C.; once the material reached 130° C., heating was continued for about 10 minutes. Then the coated sand product was allowed to cool to ambient temperature. After cooling the pH of the coated sand was adjusted to about 5.5 by spraying the sand with 15% sulfuric acid solution.

Upon microscopic examination, the coated sand product was observed to possess a uniform coating including resin, pigment and clay. When a sample of the coated sand was added to water and shaken, the coating was insoluble, but easily wettable; and no foaming was observed. Two drops of 0.5 wt % Methylene Blue dye in water was added to the coated sand in water and the slurry was shaken briefly then allowed to stand for several minutes followed by decanting the water from the sand; the sand was rinsed with clean water. The sand exhibited a purple sheen, characteristic of the association of the dye with the cation exchange sites of the clay.

Sorption and desorption of ammonium ions to/from the coated sand product was measured. A 1 g aliquot of the coated sand was added to a beaker containing about 10 mL of a 0.1 wt % ammonium sulfate solution. The sand was swirled periodically for about 30 minutes, then the liquid was decanted. The sand was washed with deionized water until no nitrogen was detected in the wash water. Then 10 mL of a 1 wt % calcium chloride solution was added to the washed sand, mixed by agitation, and the liquid decanted and analyzed. The liquid contained 40 ppm nitrogen. Sorption and desorption of ammonium ions from the exchange sites demonstrates the continued activity of the clay within the composite.

EXAMPLE 6

A 500 ml mason jar was charged with 110 g resorcinol (obtained from the Indspec Chemical Corporation of Petrolia, Pa.) and 80 g deionized water, and the mixture was stirred and warmed until the resorcinol was dissolved. Then 25 g of a 37 wt % formaldehyde solution in water was added with vigorous stirring, followed by slow addition of 1.8 g conc. $H_2SO_4$. The resulting mixture was stirred at ambient laboratory temperature for about 8 hours. Then the pH was adjusted to 5.8 using 16.5 g of a 50% w/w NaOH solution. The resultant resorcinol novalac product was found to be 57% solids.

Then 16 g of the resorcinol novalac product was removed from the jar and placed in a fresh 500 ml mason jar equipped with a magnetic stir bar; 48 g deionized $H_2O$ was added to the jar and this mixture was stirred and sparged with Argon. Then 7.4 g 50% w/w NaOH solution was added to the jar with stirring. Then 100 g MPEG 5000 Br was added slowly to the jar over 30 minutes, accompanied by vigorous stirring. After the addition was completed, stirring was continued for an additional 45 minutes. Then 329 g CASCOPHEN® OS 707M (obtained from MOMENTIVE™ Performance Materials, LLC of Columbus, Ohio) was added to the jar with vigorous stirring.

About 25 g of this mixture was removed from the flask and added to 900 g silica sand in a Cleveland-type laboratory benchtop muller and the combination was thoroughly mixed to coat the sand. Then 8 g CASCOPHEN® W3154N-1 (obtained from MOMENTIVE™ Performance Materials), 0.3 g phthalocyanine blue and 3 g BAYERFERROX® 91LO Yellow (obtained from Lanxess AG of Cologne, Germany) were added to the muller and this combination was mixed for about 1 minute. Then 70 g of PANTHER CREEK® 200 Calcium Bentonite (obtained from the American Colloid Company of Hoffman Estates, IL) was added to the muller and this combination was mixed for about 1 minute to result in a coated sand product. The coated sand product was removed from the muller and heated in an oven set at 150° C.; once the material reached 130° C., heating was continued for about 10 minutes. Then the coated sand was allowed to cool to ambient laboratory temperature. After cooling the pH of the coated sand was adjusted to about 5.5 by spraying the sand with 15% sulfuric acid solution.

Upon microscopic examination, the coated sand product was observed to possess a uniform coating including resin, pigment and clay. When a sample of the coated sand was added to water and shaken, the coating was insoluble, but easily wettable; and no foaming was observed. Two drops of 0.5 wt % Methylene Blue dye in water was added to the coated sand in water and the slurry was shaken briefly then allowed to stand for several minutes followed by decanting the water from the sand; the sand was rinsed with clean water. The sand exhibited a purple sheen, characteristic of the association of the dye with the cation exchange sites of the clay.

Sorption and desorption of ammonium ions was demonstrated using the techniques and materials of Example 5. The results were similar to the results described in Example 5.

Sorption and desorption of selected pesticides to/from the coated sand product was measured. Ten mg each of Chlorothalonil, Azoxstrobin, Paclobutrazol, and Propiconazole (all obtained from Syngenta International AG of Basel, Switzerland) were added to a single vial containing 4 ml acetone. Ten mg of a degradation product of several triazole fungicides, 1,2,4-triazole, was dissolved in 4 ml deionized water. Then 20 µL, of each of the two pesticide solutions (the water solution of 1,2,4-triazole, and the acetone solution of the Chlorothalonil, Azoxstrobin, Paclobutrazol, and Propiconazole) were added to each of six 200 ml glass vials, wherein each vial contained 10 ml of water; the vial contents were agitated to mix the contents. Four of these vials were charged with 40 g of water washed, dry coated sand product; two of these vials were charged with 40 g of the silica sand from which the coated sand products of this Example were made. The six vials were then allowed to stand for two hours with agitation every 30 minutes. Additional 15 ml aliquots of water were then added to each of the vials with agitation, then 4 ml of the liquid from each vial was decanted into a scintillation vial. Azoxstrobin, Paclobutrazol, Propiconazole, and 1,2,4-triazole were measured by LC/MS/MS using an AB SCIEX Triple Quad LC/MS/MS (obtained from the AB SCIEX Company of Framingham, Mass.); the results are shown in FIG. 1 and listed in Table 1.

TABLE 1

Increase in the measured amounts of pesticides or the metabolite 1,2,4-triazole in supernatants collected from sand vs. the coated sand product of Example 5.

| Pesticide/Metabolite | Increase conc. measured in silica sand supernatant relative to amount in coated sand supernatant (%) |
|---|---|
| 1,2,4 Triazole | 80 |
| Azoxystrobin | 827 |
| Paclobutrazol | 116 |
| Propiconazole | 664 |

Figure 2:
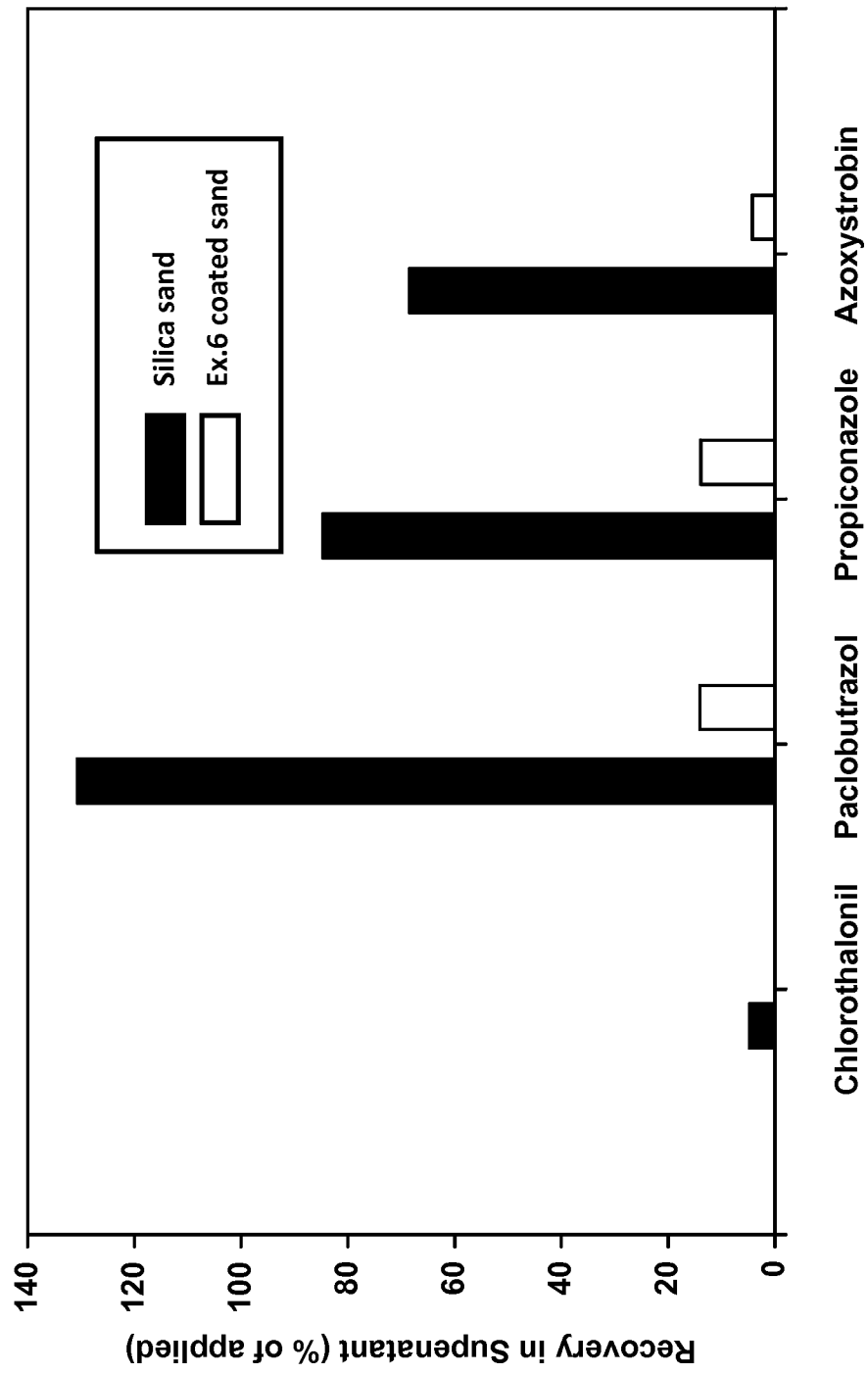
FIG. 2 is a plot of the recovery from supernatant of four different pesticides after contacting solutions of the pesticides with either silica sand or a composition of the invention.

Then 1 mL aliquots of each aqueous supernatant sample were removed and treated to replace the water with acetone in order to analyze the supernatant by GC/MS. First 1 mL acetone was added to each 1 mL supernatant aliquot with mixing. The resultant solution was evaporated under a stream of Argon at ambient laboratory temperature for 2 hours. Then 1 mL of acetone was then added to each sample and the samples were evaporated to dryness for about 4 hrs under a stream of Argon at ambient laboratory temperature. Then the dried residue was dissolved in 1 mL of acetone and analyzed via GC/MS using a Shimadzu 2010 GC/MS (obtained from the Shimadzu Corporation of Nakagyo-ku, Kyoto, Japan); the results are shown in FIG. 2.

Figure 3:
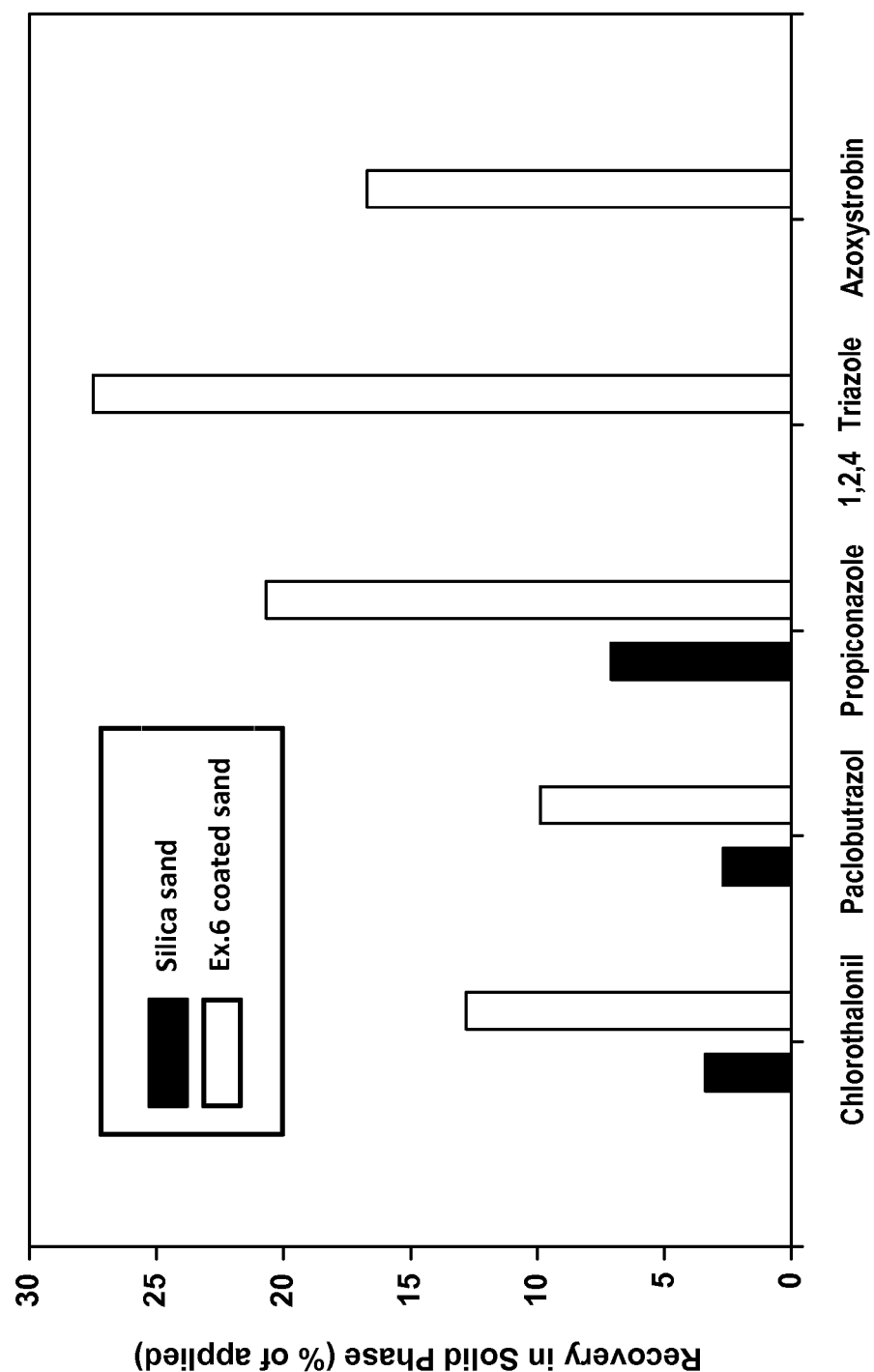
FIG. 3 is a plot of recovery of five different pesticides from either silica sand or a composition of the invention after contacting them with solutions of the pesticides.

All vials were then decanted and were rinsed once with deionized $H_2O$. Each vial was then extracted twice with 10 ml acetone, then 15 ml acetone. The acetone extracts were combined and were dehydrated similarly to the supernatant aliquots above. Four mL were decanted for analysis. Chlorothalonil, Azoxstrobin, Paclobutrazol, and Propiconazole were measured by GC/MS using a Shimadzu 2010 GC/MS (obtained from the Shimadzu Corporation of Nakagyo-ku, Kyoto, Japan); the results are shown in FIG. 3.

EXAMPLE 7

A 500 ml mason jar was charged with 110 g resorcinol (obtained from the Indspec Chemical Corporation of Petrolia, Pa.) and 80 g water, and the contents of the jar were stirred and warmed until the resorcinol was dissolved. Then 25 g of a 37 wt % aqueous solution of formaldehyde was added with vigorous stirring, followed by slow addition of 1.8 g conc. $H_2SO_4$. The resulting mixture was stirred at ambient laboratory temperature for about 8 hours. Then the pH was adjusted to 5.8 using 23.5 g of a 50% w/w KOH solution. The resultant resorcinol novalac product was found to be 57% solids.

Then 16 g of the resorcinol novalac product was removed from the jar and placed in a fresh 500 ml mason jar equipped with a magnetic stir bar; 48 g deionized $H_2O$ was added to the jar and this mixture was stirred and sparged with Argon. Then 10.6 g of the 50% KOH solution was added to the jar with stirring. Then 100 g MPEG 5000 Br was added slowly to the jar over 30 minutes, accompanied by vigorous stirring. After the addition was completed, stirring was continued for an additional 45 minutes. Then 329 g CASCOPHEN® OS 707M (obtained from MOMENTIVE™ Performance Materials, LLC of Columbus, Ohio) was added to the jar with vigorous stirring.

About 25 g of this mixture was removed from the flask and added to 900 g silica sand in a Cleveland-type laboratory benchtop muller and the combination was thoroughly mixed. Then 8 g CASCOPHEN® W3154N-1 (obtained from MOMENTIVE™ Performance Materials), 0.3 g phthalocyanine blue and 3 g BAYERFERROX® 91LO Yellow (obtained from Lanxess AG of Cologne, Germany) were added to the muller and this combination was mixed for about 1 minute. Then 70 g of PANTHER CREEK® 200 Calcium Bentonite (obtained from the American Colloid Company of Hoffman Estates, IL) was added to the muller and this combination was mixed for about 1 minute to result in a coated sand product. The coated sand product was removed from the muller and heated in an oven set at 150° C.; once the material reached 130° C., heating was continued for about 10 minutes. Then the coated sand products was allowed to cool to ambient laboratory temperature. After cooling the pH of the coated sand was adjusted to about 5.5 by spraying the sand with 15% sulfuric acid solution.

Upon microscopic examination, the coated sand product was observed to possess a uniform coating including resin, pigment and clay. When a sample of the coated sand was added to water and shaken, the coating was insoluble, but easily wettable; and no foaming was observed. Two drops of 0.5 wt % Methylene Blue dye in water was added to the coated sand in water and the slurry was shaken briefly then allowed to stand for several minutes followed by decanting the water from the sand; the sand was rinsed with clean water. The sand exhibited a purple sheen, characteristic of the association of the dye with the cation exchange sites of the clay.

Sorption and desorption of ammonium ions, and sorption and desorption of selected pesticides on the composites surface were demonstrated using the techniques and materials of Examples 5 and 6. The results were similar to those observed for Examples 5 and 6.

EXAMPLE 8

A 500 ml mason jar was charged with 16.5 g CASCOPHEN® G 1149A (obtained from MOMENTIVE™ Performance Materials, LLC of Columbus, Ohio) and 48 g deionized $H_2O$ and the mixture was sparged with Argon. Then 7.4 g 50% w/w NaOH was added with stirring. Then 100 g MPEG 5000 Br was added slowly to the jar over 30 minutes, accompanied by vigorous stirring. After the addition was completed, stirring was continued for an additional 45 minutes. Then 329 g CASCOPHEN® OS 707M (obtained from MOMENTIVE™ Performance Materials, LLC of Columbus, Ohio) was added to the jar with vigorous stirring.

About 25 g of this mixture was removed from the flask and added to 900 g silica sand in a Cleveland-type laboratory benchtop muller and the combination was thoroughly mixed. Then 8 g CASCOPHEN® W3154N-1 (obtained from MOMENTIVE™ Performance Materials), 0.3 g phthalocyanine blue and 3 g BAYERFERROX® 91LO Yellow (obtained from Lanxess AG of Cologne, Germany) were added to the muller and this combination was mixed for about 1 minute. Then 70 g of PANTHER CREEK® 200 Calcium Bentonite (obtained from the American Colloid Company of Hoffman Estates, IL) was added to the muller and this combination was mixed for about 1 minute to result in a coated sand product. The coated sand product was removed from the muller and heated in an oven set at 150° C.; once the material reached 130° C., heating was continued for about 10 minutes. Then the coated sand products was allowed to cool to ambient laboratory temperature. After cooling the pH of the coated sand was adjusted to about 5.5 by spraying the sand with 15% sulfuric acid solution.

Upon microscopic examination, the coated sand product was observed to possess a uniform coating including resin, pigment and clay. When a sample of the coated sand was added to water and shaken, the coating was insoluble, but easily wettable; and no foaming was observed. Two drops of 0.5 wt % Methylene Blue dye in water was added to the coated sand in water and the slurry was shaken briefly then allowed to stand for several minutes followed by decanting the water from the sand; the sand was rinsed with clean water. The sand exhibited a purple sheen, characteristic of the association of the dye with the cation exchange sites of the clay.

Sorption and desorption of ammonium ions, and sorption and desorption of selected pesticides on the composites surface were demonstrated using the techniques and materials of Examples 5 and 6. The results were similar to those observed for Examples 5 and 6.

EXAMPLE 9

A 1 L mason jar was charged with 80 g of the resorcinol novalac product of Example 6 and 240 g deionized $H_2O$, and the mixture was sparged with Argon. Then 37 g of 50% w/w NaOH was added with stirring. Then 500 g of MPEG 5000 Br was slowly added with stirring over 30 min, after which the mixture was stirred for another hour. Then 10 g of a 37 wt % aqueous formaldehyde solution was added to the jar. The jar was placed on a hotplate/stirrer and maintained at 55° C. under Argon blanket for 2 hours. After removing from the hotplate, 810 g of a gel-like material was recovered.

The gel was tested for formaldehyde using the PURPALD® test (reagent obtained from the Sigma-Aldrich Company of St. Louis, Mo. and used according to the manufacturer's directions). No formaldehyde was detected.

Then 270 g of the gel and 600 g deionized $H_2O$ were placed in a WARING® blender (obtained from the Conair Corp. of Stamford, Conn.) and the blender was turned to "HIGH" for 5 min. The resulting mixture was then homogenized using a rotor/stator type homogenizer. Then 6.4 g of a 69 wt % aqueous solution of (3-chloro-2-hydroxypropyl) trimethylammonium chloride (Quat 188, obtained from the Dow Chemical Company of Midland, Mich.) was added to the homogenized mixture, and this mixture was stirred overnight at 50° C. under Argon. An emulsified mixture resulted. The pH of the emulsion was adjusted to 6.0 with conc. sulfuric acid.

Adsorption of dyes by the Quat 188 gel was tested by adding 0.25 mL 0.1% bromophenol blue to a 20 mL ground gel aliquot, and adding 0.25 mL 0.1% bromothymol blue to a second 20 mL ground gel aliquot. The gel aliquots were stirred for 30 minutes, then were centrifuged at 2000 rpm for 45 min. along with water controls having the dyes dissolved therein. The resulting supernatants from the two gel aliquots were colorless and water clear. The water controls were blue.

The remainder of the gel was dried by spreading in a baking dish and placing the dish in an oven set to 50° C. until dry. The dry product was coarsely ground in a coffee grinder. The ground product was placed in a ball mill and rotated for about 48 hours to obtain a powder. The powder was used to coat pumpkin seeds, corn, and black beans using polyvinyl alcohol (PVA; MOWIOL® 10-98, obtained from the Sigma-Aldrich Company of St. Louis, Mo.) as an adhesive. Several drops of a 10 wt % PVA solution in water were placed on a glass plate, and the seeds were wetted with it and then allowed to stand at ambient laboratory temperature for about 30 min or until they developed a tacky surface. The seeds were then rolled in the powder until well coated; then the coated seeds were allowed to dry completely at ambient laboratory temperature. Uncoated seeds were germinated side by side with those coated with the powder. No difference in germination or early growth between coated and uncoated seeds were seen.

EXAMPLE 10

Unamended sphagnum peat moss was dried by placing it in an oven at 93° C. for 2 days. The dry peat exhibited strong hydrophobicity in that a drop of water placed upon the dried peat remained intact on the surface, and eventually evaporated over time without soaking into the moss fibers. Aliquots of the emulsion prepared in Example 9 corresponding to 3 g, 4.5 g, 6.0 g, and 7.5 g of solids were added to the moss by admixing each aliquot with 20 g of the moss. After the emulsion was dry, addition of a drop of water placed on the peat resulted in water drop penetration times of >10 min, >1 min, 1 min, and <10 sec respectively. No amount of additional drying of the peat sample containing 7.5 g of emulsion solids could regenerate the hydrophobicity of the original unamended and dried peat.

EXAMPLE 11

A 1 liter roundbottom flask was charged with 4.67 g of the resorcinol novalac of Example 6 and 14 g deionized $H_2O$ and the mixture was sparged with Argon. Then 2.1 g of a 50% solution of NaOH was added with stirring. Then 29 g of MPEG 5000 Br was slowly added with stirring over 30 minutes, then stirring was continued for an additional 1 hour. Then 200 ml cyclohexane and 20 g Triton X-100 (obtained from the Dow Chemical Company of Midland, Mich.) were added to the flask. The mixture was heated to reflux temperature, and during vigorous agitation under reflux conditions 0.6 g of 37 wt % aqueous formaldehyde solution was added and the temperature adjusted to maintain reflux. After two hours of stirring under reflux conditions, 200 ml of deionized $H_2O$ was added and the cyclohexane distilled from the flask. Upon cooling to ambient temperature, the remaining mixture was a stable emulsion. The emulsion was further reacted with (3-chloro-2-hydroxypropyl) trimethylammonium chloride (Quat 188), followed by pH adjustment, as described in Example 9.

EXAMPLE 12

A 1 liter mason jar was charged with of 80 g of the resorcinol novalac of Example 6 and 240 g deionized $H_2O$ and the mixture was sparged with Argon. Then 37 g of a 50% solution of NaOH was added to the mixture with stirring. Then 500 g of MPEG 5000 Br was slowly added with stirring over 30 min, and the mixture was allowed to stir for an addition 1 hour. Then 10 g of a 37% solution of formaldehyde was added to the mixture. The jar was placed on a hotplate/stirrer and maintained at 55C under Argon blanket, with stirring, for 2 hours. After cooling the mixture, 810 g of a gel-like material was recovered.

The gel was tested for formaldehyde using the PUR-PALD® test (reagent obtained from the Sigma-Aldrich Company of St. Louis, Mo. and used according to the manufacturer's directions). No formaldehyde was detected. Then 270 g of the gel and 600 g deionized $H_2O$ were placed in a WARING® blender (obtained from the Conair Corp. of Stamford, Conn.) and the blender was turned to "HIGH" for 5 min. The resulting mixture was then homogenized using a rotor/stator type homogenizer. Then 3 g formaldehyde and 3 g sodium sulfite were added to the homogenized mixture and the resulting mixture was sparged with Ar and warmed with agitation at 50° C. for 6 hours, followed by adjustment of the pH to 6.0. A stable emulsion was observed.

The emulsion adsorbed the cationic dye Methylene Blue and upon mixing was observed to have the characteristic purple color indicative of the occupation of the anionic $SO3^{2-}$ exchange sites by the dye.

CONTROL EXAMPLE A

A 250 Erlenmeyer flask was charged with 33.01 g 90% phenol, 38.78 g 37% formaldehyde, 1.2 g ZnO, and 1.8 g glacial acetic acid; these amounts correspond to a mole ratio of 1:1.5 phenol:formaldehyde. Then the flask was equipped with a condenser and placed on a hotplate stirrer and heated to reflux. The contents of the flask were refluxed for about 2 hours. Then the condenser was removed; a strong odor of formaldehyde and phenol was evident, and the viscosity of the flask had not appeared to increase noticeably. The pH of the contents was measured and was found to be 4.75. Then 75.5 g MPEG 750 (obtained from the Sigma-Aldrich Company of St. Louis, Mo.) was added to the flask and the flask was heated to 95-100° C. under simple distillation conditions for about 3.5 hours. No noticeable increase in viscosity was observed during this time; the contents of the flask were amber colored. About 24 mL of a distillate was recovered.

Figure 4:
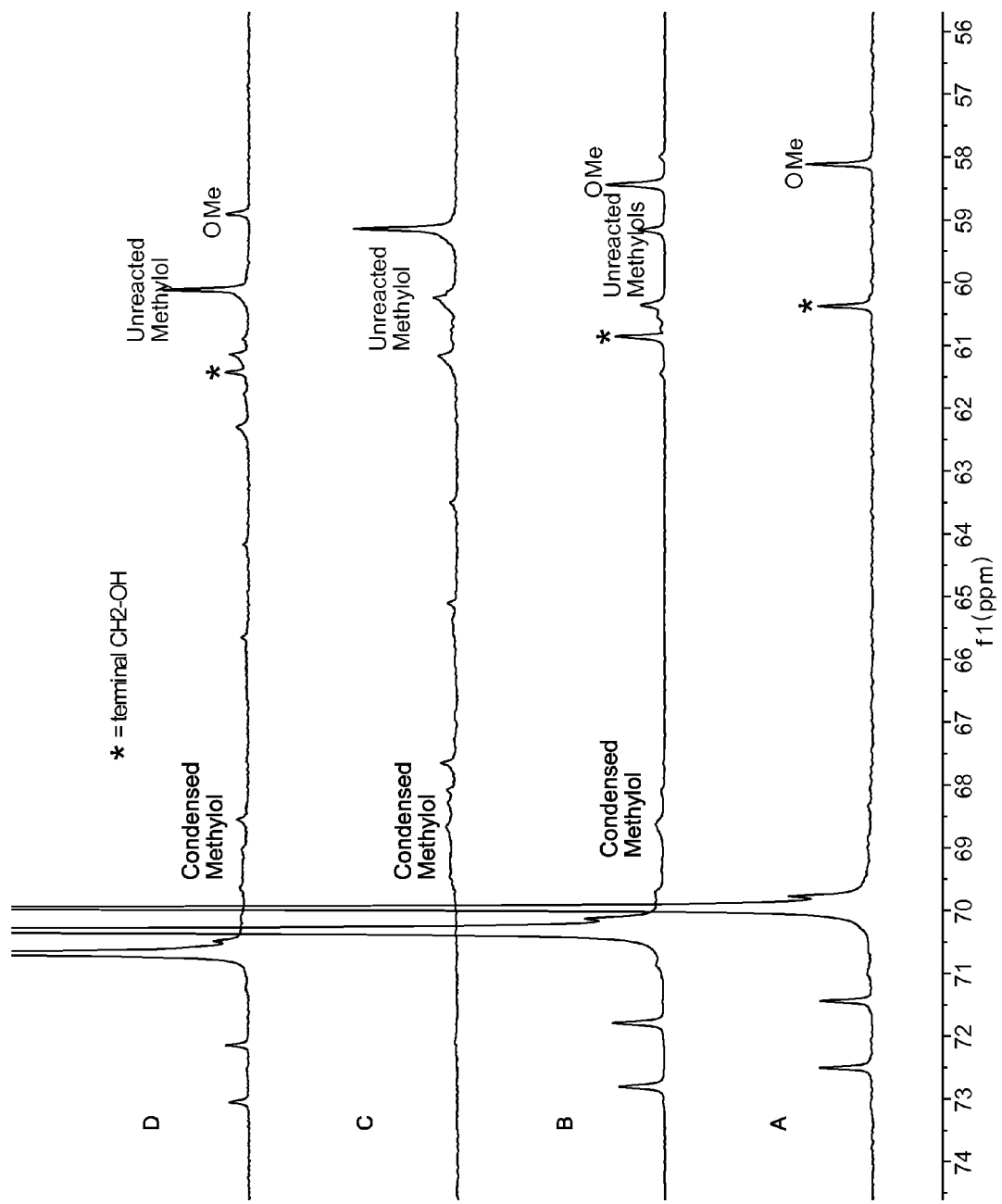
FIG. 4 is a series of $^{13}$C NMR traces for compositions of the invention and controls.

$^{13}C$ NMR (DMSO) was carried out on the contents of the flask, and $^{13}C$ NMR (DMSO) was also carried out for MPEG 750 alone. These $^{13}C$ NMR traces are shown in FIG. 4 as trace A (MPEG 750 alone), and trace B (contents of the flask). The $^{13}C$ NMR peak area was determined for peak regions corresponding to MPEG backbone carbons present in trace A at 70-71 ppm and the terminal MPEG carbon adjacent to the hydroxyl moiety present in trace A at 60.5-62 ppm. Then a ratio, Q, was determined as the ratio of backbone carbons to terminal hydroxylated carbons based on these two area calculations. Ratio $Q_A$, the ratio of backbone carbon to terminal hydroxylated carbon for MPEG detected n trace A, was calculated to be 28.54. The ratio $Q_B$ was calculated as the ratio of MPEG backbone carbon to terminal hydroxylated carbon for MPEG detected in trace B. $Q_B$ was calculated to be 27.94.

Figure 5:
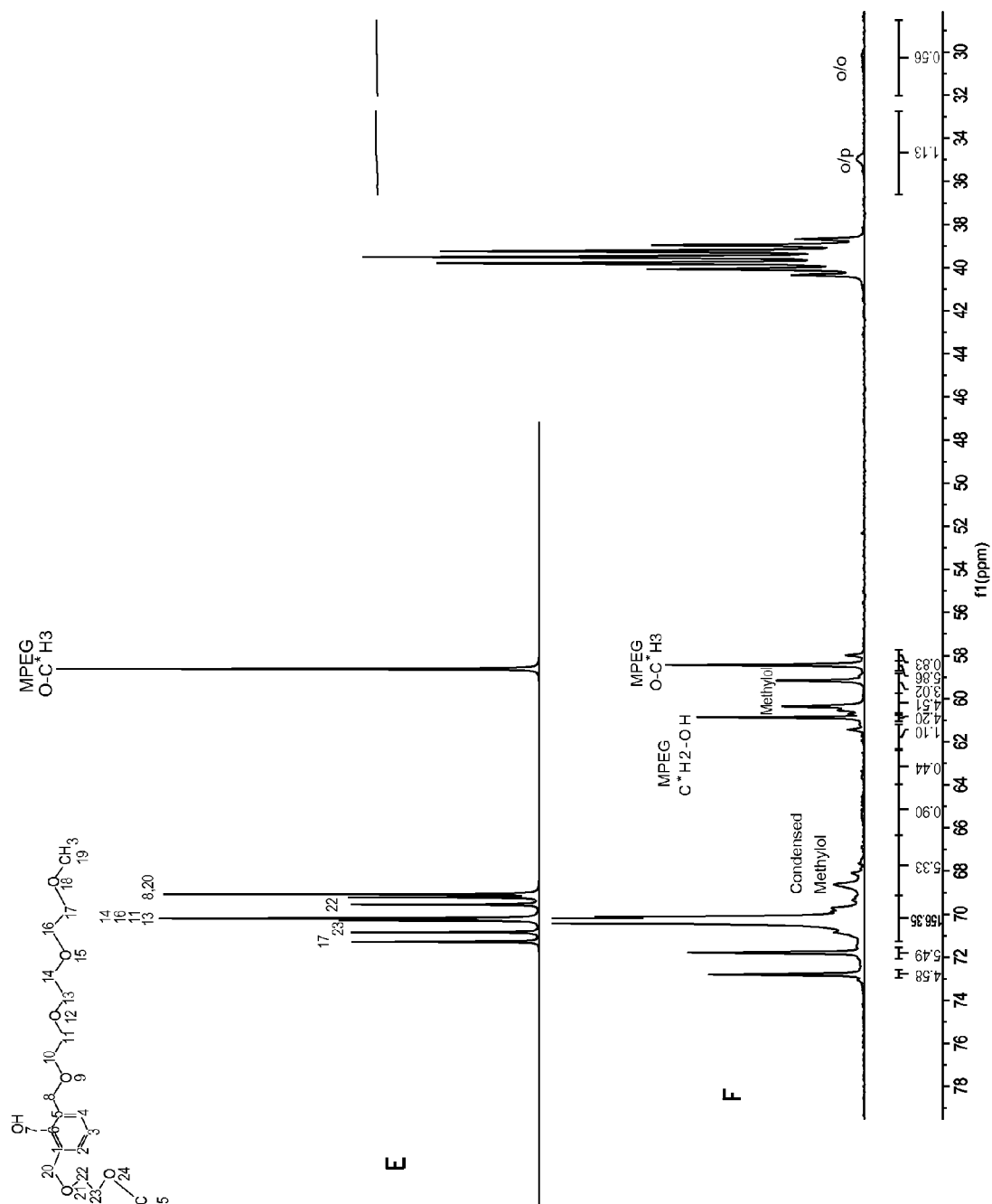
FIG. 5 is a $^{13}$C NMR trace for a composition of the invention and a theoretical $^{13}$C NMR trace for a compound.

FIG. 5 shows a theoretical $^{13}C$ NMR trace of the indicated benzyl MPEG ether structure shown, as scan E. The theoretical peaks were generated by MNova 8.1.2 NMR Software with Modgraph NMR prediction add-on (obtained from Mestrelab Research, Santiago, Spain). The theoretical trace is overlaid on the actual $^{13}C$ NMR trace of the contents of the flask, as trace F. In trace F, the absorption corresponding to the terminal hydroxylated carbon is labeled. Also labeled in trace F are absorptions attributed to aromatic methylol ether carbons present in the ortho/para (o/p) configuration vs. ortho/ortho (o/o) configuration, clearly showing that both configurations arise as a result of the reaction.

Additionally, the $^{13}C$ NMR trace of the contents of the flask showed numerous absorbances characteristic of unreacted phenol in the region of about 115 ppm to 160 ppm (not shown). Based on phenol resonances in the aromatic region, it was estimated that about 24.5% phenol moieties in the flask were unreacted.

CONTROL EXAMPLE B

A 250 Erlenmeyer flask was charged with 79.7 g (90%) phenol, 18.8 g paraformaldehyde, 0.7 g water and 0.8 g calcium acetate, and the flask was equipped with a condenser and a stir bar. These amounts correspond to a mole ratio of 1:0.82 phenol:formaldehyde. The flask was placed on a hotplate stirrer and slowly heated to reflux over a period of about 1 hour while stirring. Reflux was continued for an additional hour at which point heat was removed and 98 g of product recovered.

Then the product was split by adding 48 g of product into each of two 125 ml Erlenmeyer flasks. To one of the flasks was added 4.8 g MPEG 750 (obtained from the Sigma-Aldrich Company of St. Louis, Mo.). Both flasks were equipped with condensers and refluxed for about 2 hours. The viscosity was observed to increase substantially in both flasks. Upon cooling, both appeared as extremely viscous white products, estimated to be at least about 20 poise. The flask containing the MPEG had a minor amount of a second clear phase.

$^{13}C$ NMR (DMSO) was carried out on the contents of both flasks. These $^{13}C$ NMR scans are shown in FIG. 4 as scan C (no MPEG) and scan D (MPEG added). The Q ratio for scan D, $Q_D$, was calculated to be 24.94 using the MPEG peaks indicated in Control Example A for MPEG detected in the scan.

Figure 6:
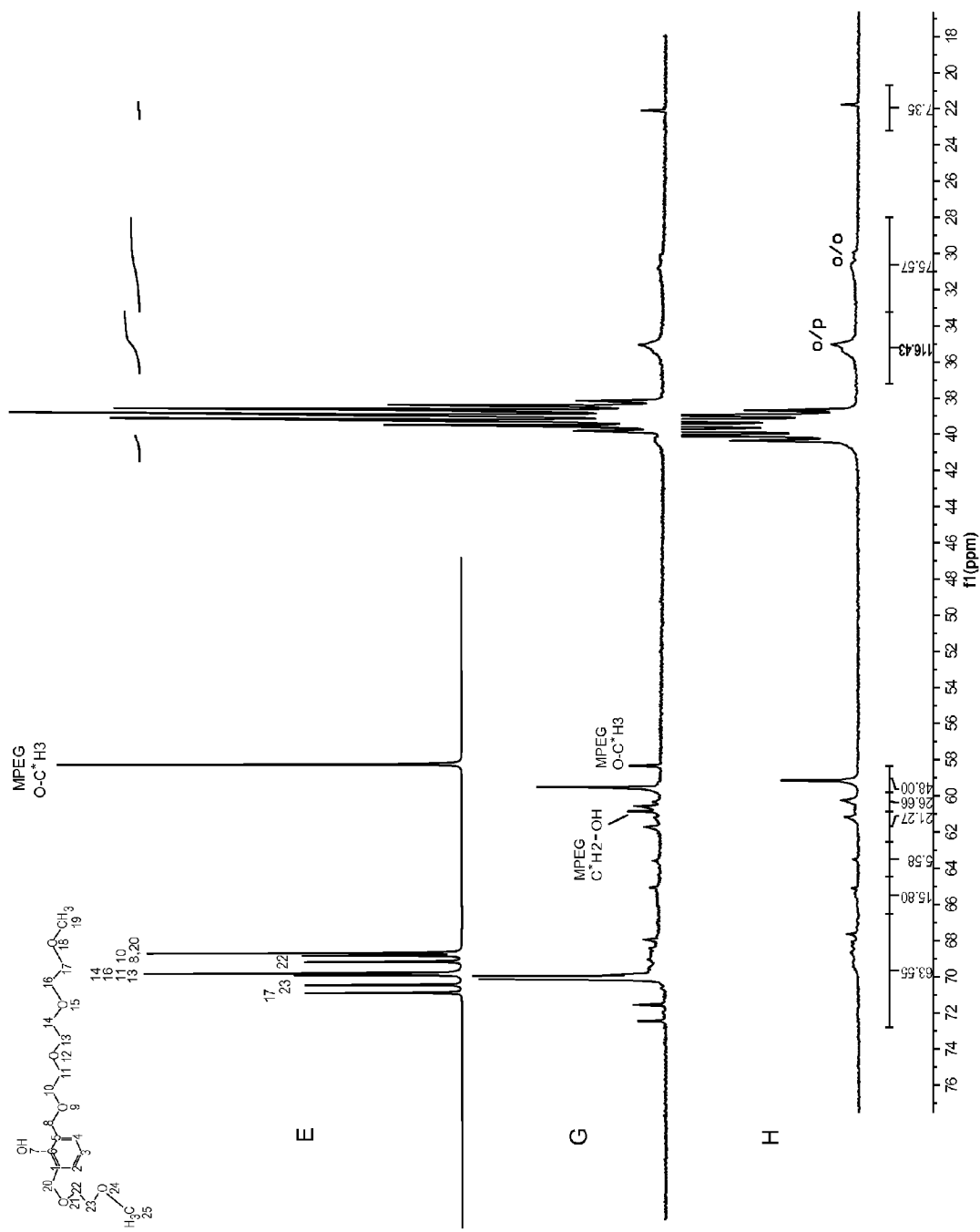
FIG. 6 is a $^{13}$C NMR trace for two compositions of the invention and a theoretical $^{13}$C NMR trace for a compound.

FIG. 6 shows the theoretical $^{13}C$ NMR trace of the indicated benzyl MPEG ether structure shown, as scan E (same theoretical trace as shown in FIG. 5). The theoretical trace is overlaid on the actual $^{13}C$ NMR trace of the contents of the flask containing MPEG, as trace G, and the contents of the flask without MPEG, as trace H. In trace G, the absorption corresponding to the terminal hydroxylated carbon of MPEG is labeled. Labeled in trace H are absorptions attributed to phenol-phenol methylol ether carbons present in the ortho/para (o/p) configuration vs. ortho/ortho (o/o) configuration, clearly showing that o/p configuration dominates the condensation in this case; these peaks are present in trace G as well and appear to be approximately the same relative size as those in trace H.

Additionally, the $^{13}$C NMR trace of the contents of the flask without MPEG showed numerous absorbances characteristic of unreacted phenol in the region of about 115 ppm to 160 ppm (not shown). Based on phenol resonances in the aromatic region, it was estimated that about 36.1% phenol moieties in the flask were unreacted.

EXAMPLE 13

A 250 mL reaction vessel was charged with 75 g MPEG 750 and 3.4 ml PBr$_3$. The contents of the vessel were stirred under Argon blanket and heated to 70° C., and maintained at 70° C. with stirring for about 3.5 hours. The product of the reaction is referred to below as "MPEG 750-Br".

Then a second vessel was charged with 110 g resorcinol and 65 ml of water; this mixture was warmed with agitation until all solids were dissolved. Then 25 g of 37% formaldehyde was added to the flask with stirring. Then 1 ml conc H$_2$SO$_4$ was added slowly to the flask. The contents of the flask were heated to 60° C. with stirring for about 2 hours. Then the pH of the contents was adjusted to 5.5 with a 50% KOH solution. The final product was an R/F novalac (resorcinol/formaldehyde novalac) The product (solution) was weighed and the weight expressed as a percent of the starting weight of the resorcinol to yield a 56% R/F novalac. The novalac was analyzed by $^{13}$C NMR. The $^{13}$C NMR trace is shown in FIG. 7, as trace J.

A third vessel was charged with 19.67 g of the R/F (resorcinol/formaldehyde) novalac (0.1 mole resorcinol), 15 mL water, and 11 mL of a 50% KOH solution. The contents of the vessel were stirred to form a homogeneous mixture and blanketed with Argon. Then the entirety of the MPEG 750-Br was added in approximately 10 mL portions with vigorous stirring over a period of about 30 minutes. After the addition was complete, the mixture was heated to 50° C. with stirring for about 2 hours. Then the pH of the mixture was adjusted to 7.5 with conc. H$_2$SO$_4$. Then the contents of the flask were centrifuged and the supernatant collected and analyzed by $^{13}$C NMR. The $^{13}$C NMR trace is shown in FIG. 7, as trace K.

Figure 7:
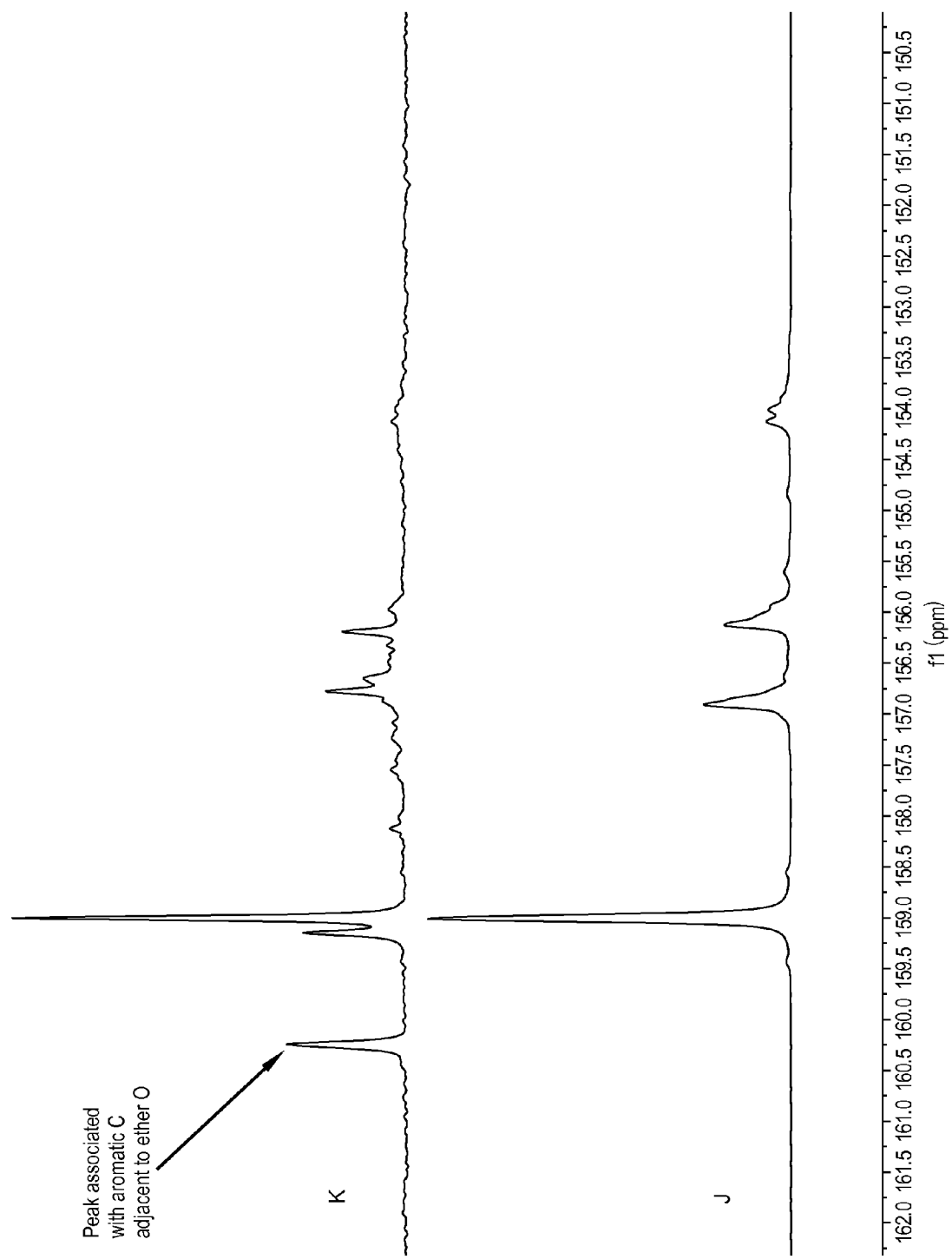
FIG. 7 is a $^{13}$C NMR trace for two compositions of the invention.

Comparison of traces J and K in FIG. 7 reveals the formation of an aromatic ether product of resorcinol and MPEG, as indicated by the peak observed at about 160.3 ppm. This peak is associated with the aromatic ether of PEG, specifically the aromatic ring carbon bonded to the ether oxygen, as determined by a theoretical absorption generated by MNova 8.1.2 NMR Software with Modgraph NMR prediction add-on (obtained from Mestrelab Research, Santiago, Spain).

EXAMPLE 14

In a first vessel, MPEG 750-Br was synthesized using the procedure of Example 13. In a second vessel, an R/F novalac having 56% resorcinol w/w was synthesized using the procedure of Example 13.

Then a third vessel was charged with 19.67 g of the R/F novalac (0.1 mole resorcinol), 11 mL 50% KOH solution, and 50 mL dimethoxypolyethylene glycol 500 (obtained from the Sigma-Aldrich Company of St. Louis, Mo.) with stirring and under Argon blanket. The mixture was heated to boiling, and a liquid was observed to distil at 110° C. Distillation was continued for about 2 hours, until distillation ceased. Then MPEG 750-Br was then added to the vessel in 10 cc portions over a period of about 0.5 hour with vigorous stirring until the entirety of the product formed above was added. The contents of the vessel were maintained at 50° C. with stirring for about 2 hours. After cooling, the pH of the contents of the vessel were adjusted to 7.5 with conc. H$_2$SO$_4$. The product was centrifuged to remove inorganic salts.

G. Representative Embodiments

While the invention is susceptible to various modifications and alternative forms, specifics thereof have been shown by way of examples, and are described in detail. It should be understood, however, that the invention is not limited to the particular embodiments described. On the contrary, the intention is to cover modifications, equivalents, and alternatives falling within the spirit and scope of the invention. In various embodiments, the invention suitably comprises, consists essentially of, or consists of the elements described herein and claimed according to the claims.

Additionally each and every embodiment of the invention, as described here, is intended to be used either alone or in combination with any other embodiment described herein as well as modifications, equivalents, and alternatives thereof falling within the spirit and scope of the invention. Representative but non-limiting embodiments and combinations thereof include the following.

A first embodiment of the invention is an ether adduct having the structure X—O—Y, wherein X is the residue of a polyhydroxylated aromatic compound, O is oxygen, and Y is a group comprising at least 10 polyalkylene oxide repeat units. In some such embodiments, X is the residue of resorcinol or a resorcinol oligomer with formaldehyde. In some such embodiments, Y is the residue of a linear polyethylene oxide; in some such embodiments the polyethylene oxide includes between 50 and 200 ethylene oxide repeat units; in some such embodiments, the polyethylene oxide comprises a methyl ether endgroup.

A second embodiment is a composition comprising the reaction product of an ether adduct and a phenolic aldehyde prepolymer, or an aldehyde, or a combination thereof, the ether adduct having the structure X—O—Y, wherein X is the residue of a polyhydroxylated aromatic compound, O is oxygen, and Y is a group comprising at least 10 polyalkylene oxide repeat units. In some such embodiments, Y is the residue of a linear polyethylene oxide having between 50 and 200 ethylene oxide repeat units and a methyl ether endgroup. In some such embodiments, X is the residue of resorcinol or a resorcinol oligomer with formaldehyde. In some such embodiments, the phenolic aldehyde prepolymer is a resole. In some such embodiments, the reaction product consists essentially of an ether adduct and an aldehyde; in some such embodiments, the reaction product is divided. In some such embodiments, the composition further comprises a fertilizer, a pesticide, an herbicide, a nematicide, two or more thereof, or a combination thereof.

A third embodiment is an article comprising particles and a composition comprising the reaction product of an ether adduct and a phenolic aldehyde prepolymer, or an aldehyde, or a combination thereof, the ether adduct having the structure X—O—Y, wherein X is the residue of a polyhydroxylated aromatic compound, O is oxygen, and Y is a group comprising at least 10 polyalkylene oxide repeat units. In some embodiments, the composition is coated on the surface of the particles. In some embodiments, the composition is present at a coating weight of about 0.1 to 25 wt % based on the weight of the uncoated particles. In some embodiments, the particle is sand. In some embodiments, the particle is clay.

In some embodiments, the article further comprises a combination of particles. In some embodiments, the particles are microparticles or nanoparticles. In some embodiments, the article further comprises a fertilizer, a pesticide, an herbicide, a nematicide, two or more thereof, a mixture thereof, or a combination thereof.

A fourth embodiment is a reactive composition comprising an ether adduct having the structure X—O—Y, wherein X is the residue of a polyhydroxylated aromatic compound, O is oxygen, and Y is a group comprising at least 10 polyalkylene oxide repeat units; a phenolic aldehyde prepolymer, an aldehyde, or a combination thereof; and a cure catalyst. In some such embodiments, the reactive composition is coated on a substrate. In some such embodiments, the substrate is a particle; in some such embodiments, the particle includes sand, clay, or a combination thereof.

A fifth embodiment is a method of forming a cured composition, the method comprising: reacting a polyhydroxylated aromatic compound with a polyalkylene oxide comprising at least an hydroxyl group and 10 polyalkylene oxide repeat units to form an ether adduct thereof; combining the ether adduct with a phenolic aldehyde prepolymer, an aldehyde, or a combination thereof, and a cure catalyst to form a reactive composition; and reacting the reactive composition to form a cured composition. In some such embodiments, the reactive composition is coated on a substrate. In some such embodiments, the ether adduct is stored for a period of time prior to forming a reactive composition, wherein the period of time is up to a month, or up to a year, or longer than a year.

I claim:

1. A composition comprising the reaction product of
   a. an ether adduct and
   b. a phenolic aldehyde prepolymer, an aldehyde, or a combination thereof, the ether adduct having the structure X—O—Y, wherein X is the residue of a polyhydroxylated aromatic compound free of methylol moieties, O is oxygen, and Y is a group comprising from about 10 to 1000 polyalkylene oxide repeat units. polyalkylene oxide repeat units.

2. The composition of claim 1 wherein Y is the residue of a linear polyethylene oxide, a linear polypropylene oxide, a mixture thereof, or a random or block copolymer thereof.

3. The composition of claim 1 wherein Y is the residue of a linear polyethylene oxide having between 50 and 200 ethylene oxide repeat units and a methyl ether endgroup.

4. The composition of claim 1 wherein X is the residue of resorcinol or a resorcinol oligomer with formaldehyde.

5. The composition of claim 1 wherein the ratio of ether adduct to phenolic aldehyde prepolymer is between about 5:1 to 1:10 by weight.

6. The composition of claim 1 wherein the phenolic aldehyde prepolymer is a resole.

7. The composition of claim 1 wherein the phenolic aldehyde prepolymer comprises a condensation product of resorcinol, phenol, or a mixture thereof with formaldehyde.

8. The composition of claim 1 wherein the reaction product consists essentially of an ether adduct and an aldehyde.

9. The composition of claim 8, wherein the reaction product is a gel cured composition, and wherein the composition is mechanically disrupted.

10. The composition of claim 1 further comprising a fertilizer, a pesticide, an herbicide, a nematicide, two or more thereof, or a combination thereof.

11. The composition of claim 1 further comprising a reactive compound.

12. An article comprising the composition of claim 1 disposed on the surface of sand particles.

13. The article of claim 12 wherein the composition of claim 1 is present at a coating weight of about 0.1 to 25 wt% based on the weight of the uncoated sand particles.

14. The coated article of claim 12 further comprising a clay.

15. The article of claim 12 further comprising a fertilizer, a pesticide, an herbicide, a nematicide, two or more thereof, a mixture thereof, or a combination thereof.

16. A reactive composition comprising
   a. an ether adduct;
   b. a phenolic aldehyde prepolymer, an aldehyde, or a combination thereof; and
   c. a cure catalyst, the ether adduct having the structure X—O—Y, wherein X is the residue of a polyhydroxylated aromatic compound free of methylol moieties, O is oxygen, and Y is a group comprising from about 10 to 1000 polyalkylene oxide repeat units.

17. The reactive composition of claim 16 wherein the reactive composition is coated on a substrate.

18. A compound having the structure X—O—Y, wherein X is the residue of a polyhydroxylated aromatic compound free of methylol moieties, O is oxygen, and Y is a group comprising from about 10 to 1000 polyalkylene oxide repeat units.

19. The compound of claim 18 wherein X is the residue of resorcinol or a resorcinol oligomer with formaldehyde.

20. The compound of claim 18 wherein Y is the residue of a linear polyethylene oxide having between 50 and 200 ethylene oxide repeat units and a methyl ether endgroup.

* * * * *

UNITED STATES PATENT AND TRADEMARK OFFICE
CERTIFICATE OF CORRECTION

PATENT NO. : 8,956,541 B2  
APPLICATION NO. : 13/913852  
DATED : February 17, 2015  
INVENTOR(S) : Curtis Elliott Page 1 of 2

It is certified that error appears in the above-identified patent and that said Letters Patent is hereby corrected as shown below:

SPECIFICATION

| Column | Line | | Should Read |
|---|---|---|---|
| 2 | 23 | "polyoxyetheralkyldiphenol" | -- polyoxyether-alkyldiphenol -- |
| 11 | 1 | 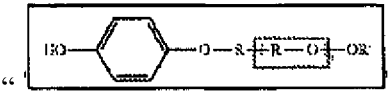 | |
| 18 | 13 | "the trade name REST-" | -- the trade name RESI- -- |
| 28 | 7 | "http:/www.usga.org" | -- http://www.usga.org -- |
| 28 | 47-48 | "http://www.ac-esag.auburn.edu" | -- http://www.acesag.auburn.edu -- |
| 28 | 49 | "http://www.missouri.edu/-extbsc/turfifundesc.htm" | -- http://www.missouri.edu/-extbsc/turf/fundesc.htm -- |
| 29 | 38 | "INSTRATAT™," | -- INSTRATA™, -- |
| 34 | 67 | "INSTRATAT™," | -- INSTRATA™, -- |
| 37 | 64 | "http:/www.usga.org/Contentaspx?id-26124" | -- http://www.usga.org/Content.aspx?id=26124 -- |
| 41 | 33 | "Then 20 µL, of each" | -- Then 20 µL of each -- |

Signed and Sealed this  
Thirtieth Day of June, 2015

Michelle K. Lee  
*Director of the United States Patent and Trademark Office*

CERTIFICATE OF CORRECTION (continued) Page 2 of 2

U.S. Pat. No. 8,956,541 B2

CLAIMS

CLAIM 1, lines 8-9

| Column | Line | | Should Read |
|---|---|---|---|
| 49 | 39 | "1000 polyaklylene oxide repeat units. polyalkylene oxide repeat units" | -- 1000 polyalkylene oxide repeat units. -- |